United States Patent
Strauss et al.

(10) Patent No.: US 6,395,892 B1
(45) Date of Patent: May 28, 2002

(54) FLORAL HOMEOTIC GENES FOR MANIPULATION OF FLOWERING IN POPLAR AND OTHER PLANT SPECIES

(75) Inventors: Steven H. Strauss, Corvallis, OR (US); William Rottmann, Summerville, SC (US); Amy Brunner, Corvallis, OR (US); Lorraine Sheppard, Davis, CA (US)

(73) Assignee: The State of Oregon Acting by and through the State Board of Higher Education on Behalf of Oregon State University, Corvallis, OR (US)

( * ) Notice: Subject to any disclaimer, the term of this patent is extended or adjusted under 35 U.S.C. 154(b) by 0 days.

(21) Appl. No.: 09/410,464

(22) Filed: Oct. 1, 1999

Related U.S. Application Data

(63) Continuation-in-part of application No. 09/287,700, filed on Apr. 6, 1999.
(60) Provisional application No. 60/080,851, filed on Apr. 6, 1998.

(51) Int. Cl.$^7$ .................. C07H 21/04; C07H 21/02; C21Q 1/68; C12P 19/34; A01H 5/00
(52) U.S. Cl. .................. 536/24.1; 435/6; 435/91.1; 435/468; 536/23.1; 800/278; 800/298
(58) Field of Search .................. 435/6, 91.1, 468, 435/375, 419; 536/23.1, 24.1, 24.5

(56) References Cited

U.S. PATENT DOCUMENTS

| | | |
|---|---|---|
| 4,795,855 A | 1/1989 | Filatti et al. |
| 5,283,184 A | 2/1994 | Jorgensen et al. |
| 5,356,799 A | 10/1994 | Fabijanski et al. |
| 5,432,068 A | 7/1995 | Albertsen et al. |
| 5,637,785 A | 6/1997 | Weigel |
| 5,659,124 A | 8/1997 | Crossland et al. |
| 5,686,649 A | 11/1997 | Chua et al. |
| 5,717,129 A | 2/1998 | Songstad et al. |

OTHER PUBLICATIONS

Roel Nusse et al., The Wnt–1 (int–1) Oncogene Promoter and Its Mechanism of Activation by Insertion of Proviral DNA of the Mouse Mammary Tumor Virus, Molecular and Cellular Biology, Aug. 1990 pp. 4170–4179.*

L. A. Sheppard, PTD: a *Populus trichocarpa* gene with homology to floral homeotic transcription factors, Thesis (199&) Oregon State University, Corvallis, OR, USA 2 (bases 1 to 4192).*

Nyers et al., "Genetic engineering of reversible sterility in trees: approaches, problems, and progress." Keystone Symposia on Molecular and Cellular Biology: The Genetic Dissection of Plant Cell Processes. Keystone, CO, Jan. 10–24, 1991. *Journal of Cellular Biochemistry*, Supplement 16A.

Rottmann et al., "Structure and expression of a LEAFY homolog from Populus." Keystone meeting, Jan 26, 1993, Taos, NM. *J. Cell. Biochem.* Suppl. 17B. p 23.

Nyers et al., "Floral MADS–box genes in poplar, pine, and Douglas–fir." Keystone Symposia on Molecular and Cellular Biology: Evolution and Plant Development, Taos, NM, Jan. 26—Feb. 10, 1993. *J. Cell. Biochem.* Suppl. 17B.

Strauss, et al., "Genetic engineering of reproductive sterility in forest trees." *Molecular Breeding* 1:5–26, 1995.

Brunner et al., "In Pursuit of the Poplar Homolog of the *Arabidopsis* Floral Homeotic Gene Agamous: Candidate for Genetic Engineering of Male and Female Reproductive Sterility." International Poplar Symposium, Program with Abstracts, University of Washington, Seattle, WA, USA, Aug. 20–25, 1995.

Han et al., "Tree Genetic Research Coooperative: Industrial Applications of Genetic Engineering to Intensive Culture of Trees." International Poplar Symposium, Program with Abstracts, University of Washington, Seattle, WA, USA, Aug. 20–25, 1995. p77.

Sheppard et al., POD is Homologous to the Floral Homeotic Gene Deficiens and is Expressed in Reproductive Primordia of both Male and Female *Populus trichocarpa* Trees. International Poplar Symposium, Program with Abstracts, University of Washington, Seattle, WA, USA, Aug. 20–25, 1995.

Sheppard et al., "Floral Homeotic Genes for Genetic engineering of Reproductive Sterility in Poplars." Somatic Cell Genetics and Molecular Genetics of Trees Meeting, Ghent, Belgium, Sep. 26–30, 1995, pp. 1–8.

Mizukami et al., "Functional Domains of the Floral Regulator Agamous: Characterization of the DNA Binding Domain and Analysis of Dominant Negative Mutations." *Plant Cell* 8:831–845, 1996.

Meilan et al., "Genetically Engineered Reproductive Sterility in Poplar." Plant Reproduction '96, 14$^{th}$ International Congress of Sexual Plant Reproduction, Cumberland Resort, Lorne, Victoria, Australia, Feb. 18–23, 1996.

Strauss et al., "Genetic Engineering of Reproductive Sterility in Forest Trees: Cloning and Expression of Three floral Homeotic Genes from Populus." Plant Reproduction '96, 14$^{th}$ International Congress of Sexual Plant Reproduction, Cumberland Resort, Lorne, Victoria, Australia, Feb. 18–23, 1996.

Brunner et al., "Characterization of *Populus* genes homologous to the *Arabidopsis* floral homeotic gene Agamous." 1996 Western Forest Genetics Association Meeting, Newport, Oregon, Jul. 29—Aug. 1, 1996, p 5.

(List continued on next page.)

Primary Examiner—Andrew Wang
Assistant Examiner—Jane Zara
(74) Attorney, Agent, or Firm—Klarquist Sparkman LLP

(57) ABSTRACT

Four floral homeotic genes from Poplar are disclosed. The disclosed nucleic acid molecules are useful for producing transgenic plants having modified fertility characteristics, particularly sterility.

26 Claims, No Drawings-

OTHER PUBLICATIONS

Han et al., "Tree Genetic Engineering Research Cooperative." 1996 Western Forest Genetics Association Meeting, Newport, Oregon, Jul. 29—Aug. 1, 1996, p 13.

Sheppard et al., "Floral Homeotic Genes for Genetic Engineering of Reproductive Sterility in Poplars: Characterization of PTD, A Poplar Homolog of Deficiens." 1996 Western Forest Genetics Association Meeting, Newport, Oregon, Jul. 29—Aug. 1, 1996, p 32.

TGERC Annual Report 1995–96, Sep. 1996, pp. 18–23.

Brunner et al., "Characterization of PTAG1 and PTAG2, two genes from *Populus trichocarpa* homologous to the *Arabidopsis* floral homeotic gene Agamaous." Pacific Division AAAS Annual Meeting, Corvallis, OR, Jun. 22–26, 1997.

TGERC Annual Report 1996–97, Aug. 1997, 18–23.

Sheppard et al., The Birds and the Bees, the Flowers and the Trees: PTD, A Deficiens Homolog from Poplar. Pacific Division AAAS Annual Meeting, Corvallis, OR Jun. 22–26, 1997.

Sheppard et al., "Cloning and Characterization of Mads–Box Genes in Black Cottonwood (*Populus Trichocarpa*)." WFGA, Vancouver, WA, Jun. 27–30, 1994.

GenBank Accession No. U93196. "*Populus balsamifera* subsp. trichocarpa Floricaula/Leafy homolog gene, complete cds." Rottmann et al.

GenBank Accession No. AF052570. "*Populus balsamifera* subsp. trichocarpa Agamous homolog (PTAG1) gene, complete cds." Brunner et al.

GenBank Accession No. AF052571. "*Populus balsamifera* subsp. trichocarpa Agamous homolog (PTAG2) gene, complete cds." Brunner et al.

GenBank Accession No. AF057708. "*Populus balsamifera* subsp. trichocarpa PTD protein (PDT) gene, complete cds." Sheppard et al.

\* cited by examiner

FLORAL HOMEOTIC GENES FOR MANIPULATION OF FLOWERING IN POPLAR AND OTHER PLANT SPECIES

CROSS REFERENCE TO RELATED APPLICATION

This is a continuation-in-part of U.S. patent application Ser. No. 09/287,700 filed Apr. 6, 1999 which claims the benefit of U.S. Provisional Application No. 60/080,851, filed Apr. 6, 1998, both of which applications are incorporated herein by reference.

FIELD OF THE INVENTION

This invention relates to nucleic acid molecules isolated from Populus species, and methods of using these molecules and derivatives thereof to produce plants, particularly trees such as Populus species, that have modified fertility characteristics.

BACKGROUND OF THE INVENTION

The increasing demand for pulp and paper products and the diminishing availability of productive forest lands are being addressed in part by efforts to develop trees that produce increased yields in shorter growth periods. Many such efforts are focused on the production of transgenic trees having modified growth characteristics, such as reduced lignin content (see for example, U.S. Pat. No. 5,451,514, "Modification of Lignin Synthesis in Plants"), and resistance to insect, viruses and herbicides. A major concern with the production of transgenic trees is the possibility that the transgenic traits might be introduced into indigenous tree populations by cross-fertilization. Thus, for example, the introduction of genes for insect resistance into indigenous tree populations could accelerate the evolution of resistant insects, adversely affect endangered insect species and interfere with normal food chains. Because of these concerns, the U.S. and other governments have instituted regulatory review processes to assess the risks associated with proposed environmental releases of transgenic plants (both for field trials and commercial production).

Genetic engineering of sterility into trees offers the possibility of securing introduced genes in the engineered tree; trees that produce neither pollen nor seeds will not be able to transmit introduced genes by normal routes of reproduction. Additional potential benefits of engineering sterility into trees include increased wood yields and reduced production of allergens such as pollen. For a review of engineering reproductive sterility in forest trees, see Strauss et al. (1995a,b).

Two primary methods for engineering sterility have been described. In the first method, termed genetic ablation, a cytotoxic gene is expressed under the control of a reproductive tissue-specific promoter. Cytotoxic genes employed in this method to date include RNase (Mariani et al., 1990; Mariani et al., 1992; Reynarts et al., 1993; Goldman et al., 1994), ADP-ribosyl transferase (Thorsness et al., 1991; Kandasamy, 1993; Thorseness et al., 1993), the Agrobacterium RoiC gene (Schmüilling, 1993), and glucanase (Worrall et al., 1992, Paul et al., 1992). The expression of the cytotoxic gene results (ideally) in the death of all cells in which the reproductive tissue-specific promoter is active. It is therefore critical that the promoter be highly specific to the reproductive tissue to avoid pleiotropic effects on vegetative tissue. For this reason, genome position effects on the transgene need to be monitored (see Strauss et al., 1995a,b).

The success of genetic ablation methods in trees will thus depend on the availability of a suitable reproductive tissue-specific promoter for the tree species in question.

The second method for engineering sterility involves inhibiting the expression of genes that are essential for reproduction. This can be accomplished in a number of ways, including the use of antisense RNA, sense suppression and promoter-based suppression. Details and applications of antisense (Kooter, 1993; Mol et al., 1994; Van der Meer et al., 1992; Pnueli et al., 1994), sense suppression (Flavell, 1994; Jorgensen, 1992; Taylor et al., 1992) and promoter-based suppression (Brusslan et al., 1993; Matzke et al., 1993) technologies in plants have been described in the scientific literature. The key to the use of any of these methods in the production of sterile trees is the identification of appropriate indigenous genes, i.e, disruption of the expression of such genes must result in the abolition of correct reproductive tissue development.

Genes specifically expressed in reproductive tissues have been isolated from a number of plant species (for a review, see Strauss et al., 1995a). Genes that have been characterized as acting early in the development of floral structures include LEAFY (LFY) from Arabidopsis (Weigel et al., 1992), APETALAI (AP1) from Arabidopsis (Mandel et al, 1992a,b), and FLORICAULA (FLO) from Antirrhinum (Coen et al., 1990), which regulate the transition from inflorescence to floral meristems. APETALA2 (AP2) appears to regulate the AGAMOUS gene (AG) which plays a role in differentiation of male and female floral tissues (see Okamuro et al., 1993). DEFICIENS (DEF) is a floral homeotic gene from Antirrhinum that is expressed throughout flower development (Schwarz-Sommer et al. 1992).

The majority of floral homeotic genes are members of the MADS-box family of transcription factors (Yanofsky et al., 1990). The MADS-box is a conserved region of approximately 60 amino acid residues. MADS is an acronym for the first four known genes in which the MADS-box was identified: yeast minichromosomal maintenance factor (MCM1), the floral homeotic genes AG and DEF, and human serum response factor (SRF). Plant MADS-box genes contain four domains: the highly conserved MADS-box region located near or at the 5' end of the translated region in plant genes; the L or linker region between the MADS and K domains; the K domain, a moderately conserved keratin-like region predicted to form amphipathic α-helices; and a highly variable carboxy-terminal region. The K-box is only present in plant MADS-box genes. It is thought to be involved in protein-protein interactions (Pnueli et al., 1991).

Studies have shown that the organization of the MADS domain in plants is similar to that in SRF; the basic N-terminal portion of the domain is required for DNA-binding and the C-terminal half of the box is required for dimerization. Because MADS proteins bind DNA as dimers, the MADS box as well as a C-terminal extension that is involved in dimerization are required for DNA-binding. The C-terminal extension varies throughout the gene family. C-terminal deletions indicate that the minimal DNA-binding domain of AP1 and AG includes the MADS-box and part of the L region, whereas AP3 and PI require a portion of the K box in addition to the MADS and L regions (Riechmann et al., 1996). The difference in the sizes of the minimal binding domains is thought to reflect the dimerization characteristics of the respective proteins: AP1 and AG bind DNA as homodimers whereas AP3/PI and their Antirrhinum homologs DEF/GLO bind as heterodimers.

MADS-box proteins have been found to bind to a motif found in target gene promoters referred to as the CArG-box.

CArG-box motifs are also found in the promoters of MADS-box genes, where they are thought to be targets for auto-regulation. Riechmann et al. (1996) used circular permutation and phasing analysis to detect conformational changes in DNA that resulted from MADS-box protein binding (Reichmann et al., 1996). They found that bound AP1, AP3/PI, and AG all induce DNA bending oriented toward the minor groove. For a review of MADS box biology, see Ma, 1994; Purugganan et al., 1995; and Yanofsky, 1995. AG and DEF have been characterized as MADS box genes; while FLO and LFY appear to encode transcription factors and have proline-rich and acidic domains, they are not MADS box genes.

Following a functional analyses of MADS box genes, Mizukami et al. (1996) created deletion mutants of AG in which various domains of the gene, including the MADS and K boxes were deleted. Based on their results, they proposed that dominant negative mutations of MADS box genes could be created by deleting the all or part of the MADS domain, or by deleting all or part of the K domain or by deleting various portions of the 3' region of the AG open reading frame. It was proposed that the proteins encoded by these deletion mutants would be able to bind either the target DNA (i.e., the nucleotide sequence to which the transcription factor binds) or the protein co-factors required for transcription, but not both. Thus, it was proposed that such mutant proteins would interfere with the functioning of the coexisting corresponding endogenous gene. The studies of floral homeotic genes discussed in the preceding paragraphs have been primarily undertaken in model plants such as Arabidopsis and Antirrhinum; few, if any, studies have addressed the genetics of flowering in tree species at the molecular level.

Species of the genus Populus are becoming increasingly important in the forestry industry, particularly for pulp and paper production, in part because of their fast growth characteristics. This group includes aspens (species of Populus section Leuce and their hybrids), and hybrids between black cottonwood (*P. trichocarpa* Torr. and Gray, also classified as *P. balsamifera* subsp. *trichocarpa*; Brayshaw, 1965) and eastern cottonwood (*P. deltoides* L.). These species are also well suited to manipulation by genetic engineering because they are fast-growing, have relatively small genomes, are easy to regenerate in vitro, and are susceptible to transformation with Agrobacterium. To date however, relatively few genes have been cloned from these species. Notably, the genetic basis underlying floral development in these species is alnost completely uncharacterized.

Floral development in the genus Populus is significantly different from what is seen in a typical hermaphroditic annual (Nagaraj, 1952; Boes and Strauss, 1994). The apices of the branches do not become inflorescences. The flowers are borne on axillary inflorescences, or catkins, with male and female flowers found on separate trees, although occasionally mixed inflorescences or hermaphroditic flowers are seen. The inflorescences appear from dormant buds in the spring, usually occurring from about five years of age. Instead of the usual structure of four concentric whorls of organs (sepals outermost, followed by petals, then stamens surrounding one or more carpels in the center), the Populus flower apparently has only two whorls (a reduced perianth cup surrounding either stamens or carpels). Unlike several other species that produce unisexual flowers through developmental arrest or degeneration of one set of organs (Cheng et al., 1983; Grant et al., 1994), Populus does not initiate male organs in female flowers or vice versa (Boes and Strauss, 1994; Sheppard, 1997). After releasing pollen or seeds, the entire inflorescences are shed (Kaul, 1995). By late spring, the inflorescence buds for the next year's flowers have already been initiated in the axils of the current year's leaves, and will develop for several more months before going dormant.

The availability of genes that control floral development in Populus species would permit the production of genetically engineered sterile trees. In turn, the ability to control fertility of Populus trees in this way would be of great value in environmental and biosafety of Populus trees engineered for improved agronomic characteristics. It is to such genes that the present invention is directed.

SUMMARY OF THE INVENTION

The present invention provides four floral homeotic genes from *Populus trichocarpa*. The four genes are herein termed PTLF, PTD, PTAG-1 and PTAG-2. These genes are homologs of floral homeotic genes isolated from other plant species. Specifically, PTLF is a homolog of LEAFY (LFY) and FLORICAULA (FLO), PTD is a homolog of DEFICIENS (DEF) and PTAG-1 and PTAG-2 are homologs of AGAMOUS (AG). The Populus genes are shown to be expressed in floral tissues; for example, PTLF is expressed in immature inflorescences on which floral promordia are developing, whereas PTD is expressed strongly in stamen primordia from the onset of organogenesis. PTD is also expressed at low levels in carpel primordia.

The invention provides the nucleic acid sequences of these four Populus genes, the corresponding cDNA sequences and the deduced amino acid sequences of the encoded polypeptides. Along with these sequences, the present invention also provides methods of using the gene and cDNA sequences to produce genetically engineered Populus species and other trees having modified fertility characteristics, including sterility.

Genetic constructs useful in producing genetically engineered Populus and other trees include antisense versions of PTLF, PTD, PTAG-1 and PTAG-2, dominant negative mutants of these genes, and constructs useful for sense suppression. In addition, the promoter sequences of these genes may be used to obtain floral-specific expression of genes such as cytotoxins that may be employed in genetic ablation strategies to produce trees having modified fertility characteristics, including sterility.

In one aspect, the invention provides isolated nucleic acid molecules comprising portions of the disclosed nucleic acid sequences. Such molecules comprise at least 15 consecutive nucleotides of the disclosed PTLF, PTD, PTAG-1 or PTAG-2 nucleic acid sequences, and may be longer, comprising at least 20, 25, 50, or 100 consecutive nucleotides of these sequences. Such molecules are useful, among other things, as primers and probes for amplifying all or parts of the disclosed sequences and for detecting the expression of the nucleic acid molecules in cells, such as cells of transgenic plants. Thus, in one aspect, such molecules are useful to monitor the expression of transgenes comprising some portion of the PTD, PTLF, PTAG-1 or PTAG-2 molecules.

Modification of the fertility traits of plants, such as Populus species may also be obtained by introducing genetic constructs containing variants of all or portions of the disclosed PTD, PTLF, PTAG-1 or PTAG-2 sequences. Such variants are provided by the invention and may comprise a nucleotide sequence of at least 50 (or, for example, at least 100) nucleotides in length which sequence hybridizes under stringent conditions to the disclosed nucleic acid sequences.

Alternatively, such variants may share a specified percentage of sequence identity with the disclosed nucleic acid sequences (e.g., at least 75% or at least 90% sequence identity) as determined using a specified sequence alignment program.

The disclosed nucleic acid molecules and variant forms of these molecules may be assembled in nucleic acid vectors for introduction into cells, such as plant cells. Thus, another aspect of the invention comprises the disclosed nucleic acid molecules and variants thereof, and vectors comprising these molecules.

In another embodiment, the invention provides transgenic plants comprising the vectors. Such transgenic plants may have altered phenotypes (compared to non-transgenic plants of the same species) including modified fertility characteristics. Modified fertility characteristics include modifications in the timing of flowering, for example, advancing the timing of flowering relative to non-transgenic plants of the same species, and sterility. Sterility may be complete sterility, or may be male only or female only sterility. Examples of transgenic plants provided by the present invention include genetically engineered sterile Populus and Eucalyptus species.

In another embodiment, the invention provides transgenic plants that comprise a recombinant expression cassette, wherein the recombinant expression cassette comprises a promoter sequence operably linked to a first nucleic acid sequence, and wherein the first nucleic acid sequence comprises all or part of one of the disclosed nucleic acid molecules, or a variant of one of the disclosed nucleic acid molecules. By way of example, such transgenic plants include plants in which the first nucleic acid is arranged in reverse orientation to the promoter sequence in the recombinant expression cassette, such that an antisense RNA is produced. In another example, such transgenic plants include plants in which the first nucleic acid is a dominant negative mutant of PTD, PTLF, PTAG-1 or PTAG-2, produced by deletion of part of the coding region, such as the 3' portion of the open reading frame, or all or part of a MADS or K-box region of the coding region. In other embodiments, the promoter sequence driving expression of the first nucleic acid may be a promoter that confers enhanced expression of the first nucleic acid molecule in floral tissues of the plant relative to non-floral tissues.

In other embodiments, the expression of at least one endogenous gene in transgenic plants containing such a recombinant expression cassette will be modified as a result of the cassette. In particular embodiments, that modified expression will affect the fertility of the plant, and will render the plant sterile.

In yet other embodiments, the invention provides transgenic plants comprising a recombinant expression cassette, wherein the recombinant expression cassette comprises a promoter sequence operably linked to a first nucleic acid sequence, and wherein the promoter sequence is a promoter sequence from PTD, PTLF, PTAG-1 or PTAG-2. In particular embodiments, the first nucleic acid sequence encodes a cytotoxic polypeptide.

These and other aspects of the invention are described in more detail below.

SEQUENCE LISTING

The nucleic and amino acid sequences listed in the accompanying Sequence Listing are showed using standard letter abbreviations for nucleotide bases, and three letter code for amino acids. Only one strand of each nucleic acid sequence is shown, but the complementary strand is understood to be included by any reference to the displayed strand.

Seq. I.D. No. 1 shows the nucleic acid sequence of the PTD gene. The sequence comprises the following regions:

| Nucleotide numbers | Feature |
| --- | --- |
| 1–1872 | 5' regulatory region |
| 1752–1756 | probable CAAT box |
| 1782–1786 | probable CAAT box |
| 1845–1851 | probable TATA box |
| 1873–2188 | Exon 1 (including inferred 5' UTR) |
| 2189–2327 | Intron 1 |
| 2328–2394 | Exon 2 |
| 2395–2484 | Intron 2 |
| 2485–2546 | Exon 3 |
| 2547–2652 | Intron 3 |
| 2653–2752 | Exon 4 |
| 2753–3309 | Intron 4 |
| 3310–3351 | Exon 5 |
| 3352–3432 | Intron 5 |
| 3433–3477 | Exon 6 |
| 3478–3584 | Intron 6 |
| 3585–4000 | Exon 7 |
| 3765–4285 | 3' regulatory region (including 3' UTR) |
| 3765–4000 | 3' UTR |

Seq. I.D. No. 2 shows the nucleic acid sequence of the PTD cDNA.

Seq. I.D. No. 3 shows the nucleic acid sequence of the PTD ORF.

Seq. I.D. No. 4 shows the amino acid sequence of the PTD polypeptide. The sequence comprises the following regions:

| Amino Acid numbers | Feature |
| --- | --- |
| 1–57 | MADS domain |
| 87–154 | K-domain |

Seq. I.D. No. 5 shows the nucleic acid sequence of the PTLF gene. The sequence comprises the following regions:

| Nucleotide numbers | Feature |
| --- | --- |
| 1–2638 | 5' regulatory region |
| 2477–2481 | probable CAAT box |
| 2536–2542 | probable TATA box |
| 2568–2574 | probable TATA box |
| 2628–3074 | Exon 1 |
| 3075–3655 | Intron 1 |
| 3656–3990 | Exon 2 |
| 3991–4679 | Intron 2 |
| 4680–5197 | Exon 3 |
| 5043–5197 | 3' UTR |
| 5043–5656 | 3' regulatory region (including 3' UTR) |

Seq. I.D. No. 6 shows the nucleic acid sequence of the PTLF cDNA.

Seq. I.D. No. 7 shows the nucleic acid sequence of the PTLF ORF.

Seq. I.D. No. 8 shows the amino acid sequence of the PTLF polypeptide.

Seq. I.D. No. 9 shows the nucleic acid sequence of the PTAG-1 gene. The sequence comprises the following regions:

| Nucleotide numbers | Feature |
| --- | --- |
| 1–2410 | 5' regulatory region |
| 2411–2588 | Exon 1 |
| 2589–3056 | Intron 1 |
| 3057–3296 | Exon 2 |
| 3297–8161 | Intron 2 |
| 8162–8243 | Exon 3 |
| 8244–8894 | Intron 3 |
| 8895–8956 | Exon 4 |
| 8957–9041 | Intron 4 |
| 9042–9141 | Exon 5 |
| 9142–9284 | Intron 5 |
| 9285–9326 | Exon 6 |
| 9327–9529 | Intron 6 |
| 9530–9571 | Exon 7 |
| 9572–9711 | Intron 7 |
| 9712–9878 | Exon 8 |
| 9879–10930 | Intron 8 |
| 10931–11215 | Exon 9 |
| 10935–11485 | 3' regulatory region (including 3' UTR) |
| 10935–11215 | 3' UTR |

Seq. I.D. No. 10 shows the nucleic acid sequence of the PTAG-1 cDNA.

Seq. I.D. No. 11 shows the nucleic acid sequence of the PTAG-1 ORF.

Seq. I.D. No. 12 shows the amino acid sequence of the PTAG-1 polypeptide. The sequence comprises the following regions:

| Amino Acid numbers | Feature |
| --- | --- |
| 17–72 | MADS domain |
| 106–172 | K-domain |

Seq. I.D. No. 13 shows the nucleic acid sequence of the PTAG-2 gene. The sequence comprises the following regions:

| Nucleotide numbers | Feature |
| --- | --- |
| 1–2336 | 5' regulatory region |
| 2118–2122 | probable CAAT box |
| 2256–2262 | probable TATA box |
| 2337–2421 | Exon 1 |
| 2422–2913 | Intron 1 |
| 2914–3153 | Exon 2 |
| 3154–7035 | Intron 2 |
| 7036–7117 | Exon 3 |
| 7118–7946 | Intron 3 |
| 7947–8008 | Exon 4 |
| 8009–8094 | Intron 4 |
| 8095–8194 | Exon 5 |
| 8195–8331 | Intron 5 |
| 8332–8373 | Exon 6 |
| 8374–8529 | Intron 6 |
| 8530–8571 | Exon 7 |
| 8572–8700 | Intron 7 |
| 8701–8863 | Exon 8 |
| 8864–9396 | Intron 8 |
| 9397–9691 | Exon 9 |
| 8863–10007 | 3' regulatory region (including 3' UTR) |
| 8863–8863 joined to 9397–9691 | 3' UTR |

Seq. I.D. No. 14 shows the nucleic acid sequence of the PTAG-2 cDNA.

Seq. I.D. No. 15 shows the nucleic acid sequence of the PTAG-2 ORF.

Seq. I.D. No. 16 shows the amino acid sequence of the PTAG-2 polypeptide. The sequence comprises the following regions:

| Amino Acid numbers | Feature |
| --- | --- |
| 16–72 | MADS domain |
| 106–172 | K-domain |

Seq. I.D. Nos. 17–24 show oligonucleotide primers that may be used to amplify portions of the disclosed floral homeotic nucleic acid sequences.

DETAILED DESCRIPTION OF THE INVENTION

I. Definitions and Abbreviations

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

cDNA (complementary DNA): A piece of DNA lacking internal, non-coding segments (introns). cDNA is synthesized in the laboratory by reverse transcription from messenger RNA extracted from cells.

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Ortholog: Two nucleotide or amino acid sequences are orthologs of each other if they share a common ancestral sequence and diverged when a species carrying that ancestral sequence split into two species. Orthologous sequences are also homologous sequences.

Probes and primers: Molecules useful as nucleic acid probes and primers may readily be prepared based on the nucleic acids provided by this invention. Typically, but not necessarily, such molecules are oligonucleotides, i.e., linear nucleic acid molecules of up to about 100 nucleotides bases in length. However, longer nucleic acid molecules, up to and including the full length of a particular floral homeotic gene may also be employed for such purposes.

A nucleic acid probe comprises at least one copy (and typically many copies) of an isolated nucleic acid molecule of known sequence that is used in a nucleic acid hybridization protocol. Generally (but not always) the nucleic acid molecule is attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, usually DNA oligonucleotides 8–10 nucleotides or more in length, and more typically 15–25 nucleotides in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the cDNA disclosed in Seq. I.D. No. 2 will anneal to a target sequence such as a homologous sequence in Eucalyptus contained within a Eucalyptus cDNA library with a higher specificity than a corresponding primer of only 15 nucleotides. Thus, in order to obtain greater specificity, probes and primers may be selected that comprise 20, 25, 30, 35, 40, 50, 75, 100 or more consecutive nucleotides of the disclosed nucleic acid sequences.

The invention thus includes isolated nucleic acid molecules that comprise specified lengths of the disclosed floral homeotic sequences. Such molecules may comprise at least 8–10, 15, 20, 25, 30, 35, 40, 50, 75, or 100 consecutive nucleotides of these sequences and may be obtained from any region of the disclosed sequences. By way of example, the floral homeotic genes shown in the Sequence Listing may be apportioned into halves or quarters based on sequence length, and the isolated nucleic acid molecules may be derived from the first or second halves of the molecules, or any of the four quarters. The PTD cDNA, shown in Seq. I.D. No. 2 may be used to illustrate this. This cDNA is 924 nucleotides in length and so may be hypothetically divided into halves (nucleotides 1–462 and 463–924) or quarters (nucleotides 1–231, 232–462, 463–693 and 694–924). Nucleic acid molecules may be selected that comprise at least 8–10, 15, 20, 25, 30, 35, 40, 50, 75 or 100 consecutive nucleotides of any of these portions of the floral homeotic genes. Thus, one such nucleic acid molecule might comprise at least 25 consecutive nucleotides of the region comprising nucleotides 1–924 of the disclosed floral homeotic genes.

Purified: The term purified does not require absolute purity; rather, it is intended as a relative term. Thus, for example, a purified PTAG-1 protein preparation is one in which the PTAG-1 protein is more pure than the protein in its natural environment within a cell. Generally, a preparation of a floral homeotic protein is purified such that the floral homeotic protein represents at least 5% of the total protein content of the preparation. For particular applications, higher purity may be desired, such that preparations in which the floral homeotic protein represents at least 50% or at least 75% of the total protein content may be employed.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Transformed: A transformed cell is a cell into which has been introduced a nucleic acid molecule by molecular biology techniques. As used herein, the term transformation encompasses all techniques by which a nucleic acid molecule might be introduced into such a cell, including Agrobacterium-mediated transformation, transfection with viral vectors, transformation with plasmid vectors and introduction of naked DNA by electroporation, lipofection, and particle gun acceleration.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Sequence identity: the relatedness of two nucleic acid sequences, or two amino acid sequences is typically expressed in terms of the identity between the sequences (in the case of amino acid sequences, similarity is an alternative assessment). Sequence identity is frequently measured in terms of percentage identity; the higher the percentage, the more similar the two sequences are. Homologs of a disclosed floral homeotic protein or nucleic acid sequence will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at http://www.ncbi.nlm.nih.gov/BLAST/. A description of how to determine sequence identity using this program is available at http://www.ncbi.nlm.nih.gov/BLAST/blast help.html.

Homologs of the disclosed floral homeotic proteins are typically characterized by possession of at least 50% sequence identity counted over the full length alignment with the amino acid sequence of a selected floral homeotic protein using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described at http://www.ncbi.nlm.nih.gov/BLAST/blast FAQs.html. One of skill in the art will appreciate that these sequence identity ranges are provided for guidance only; it is entirely possible that strongly significant homologs could be obtained that fall outside of the ranges provided. The present invention provides not only the peptide homologs as described above, but also nucleic acid molecules that encode such homologs.

Homologs of the disclosed floral homeotic nucleic acids are typically characterized by possession of at least 50% sequence identity counted over the fall length alignment with the nucleic acid sequence of a selected floral homeotic gene using the NCBI Blast 2.0, blastn set to default parameters. Homologs with even greater similarity to the reference sequences will show increasing percentage identities when assessed by this method, such as at least 60%, at least 65%, at least 70%, at least 75%, at least 80%, at least 90% or at least 95% sequence identity.

An alternative indication that two nucleic acid molecules are closely related is that the two molecules hybridize to each other under stringent conditions. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Nucleic acid molecules that hybridize under stringent conditions to a disclosed nucleic acid sequences will typically hybridize to a probe corresponding to either the entire cDNA or selected portions of the cDNA under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequence that all encode substantially the same protein.

Floral Specific Promoter: As used herein, the term "floral specific promoter" refers to a regulatory sequence which confers gene expression only in, or predominantly in, floral tissues. The complete sequences of four floral specific promoters are disclosed herein: the promoter of PTD, located within the 5' regulatory region comprising nucleotides 1–1872 of Seq. I.D. No. 1; the promoter of PTFL, located within the 5' regulatory region comprising nucleotides 1–2638 of Seq. I.D. No. 5; the promoter of PTAG-1, located within the 5' regulatory region comprising 1–2410 of Seq. I.D. No. 9; and the promoter of PTAG-2, located within the 5' regulatory region comprising nucleotides 1–2336 of Seq. I.D. No. 13). Accordingly, these promoter sequences may be used to produce transgene constructs that are specifically or predominantly expressed in floral tissues. One of skill in the art will recognize that effective floral-specific expression may be achieved with less than the entire promoter sequences noted above. Thus, by way of example, floral-specific expression may be obtained by employing sequences comprising 500 nucleotides or fewer (e.g., 250, 200, 150, or 100 nucleotides) upstream of the start codon, AUG, of the disclosed gene sequences.

The determination of whether a particular sub-region of the disclosed sequences operates to confer floral specific expression in a particular system (taking into account the plant species into which the construct is being introduced, the level of expression required, etc.), is preformed using known methods, such as operably linking the promoter sub-region to a marker gene (e.g. GUS), introducing such constructs into plants and then determining the level of expression of the marker gene in floral and other plant tissues. Sub-regions which confer only or predominantly floral expression, are considered to contain the necessary elements to confer floral specific expression.

II. Methods

The four floral homeotic genes were obtained, and the present invention can be practiced, using standard molecular biology and plant transformation procedures, unless otherwise noted. Standard molecular biology procedures are described in Sambrook et al (1989), Ausubel et al. (1987) and innis et al. (1990).

III. Isolation and Characterization of PTLF

Genomic DNA was purified from dormant vegetative buds of a single *Populus trichocarpa* tree using a modified CTAB extraction technique (Wagner et al., 1987). After centrifugation to pellet nuclei, a large gummy pellet of resin was evident. This was left intact during the resuspension of nuclei, and then discarded. Normal yield of DNA was approximately 1 mg per 40 g of tissue. A genomic library was constructed from DNA partially digested with Sau3A, filled in with DNA Pol I and DATP and dGTP, and ligated into LambdaGem-12 vector (Stratagene) having partially filled-in Xho I sites. Packaging of the DNA into phage particles was performed with GigaPack Gold II (Stratagene).

RNA was extracted using the lithium dodecyl sulfate method of Baker et al. (1990), and purified by centrifugation through a 5.7 M CsCl pad. After redissolving the RNA pellet in TE, pH 8.0, NaCl was added to 400 mM and the RNA was precipitated with EtOH to remove excess CsCl. PolyA$^+$ RNA was selected using oligo dT-cellulose columns (mRNA Separation Kit, Clontech). RNA was stored at −80° C. until use. Ten-microgram samples of total RNA were used as templates for single-stranded cDNA synthesis. Reactions included 50 mM TrisHCl (pH 8.3), 75 mM KCl, 10 mM dithiothreitol, 3 mM MgCl$_2$, 100 µM each dNTP, 4 µg primer XT, 10 µCi [α$^{32}$P]-dCTP, and 200 U M-MLV reverse transcriptase (Gibco BRL) in 50 µL. Incubations were performed at 37° C. for 1 hr, then the cDNA was purified with GeneClean (BIO101) silica matrix. Typical yields were 10–40 ng of cDNA, as determined by $^{32}$P incorporation. The size ranges of the cDNA samples were characterized by alkaline gel electrophoresis. cDNA products were between 500 to 4000 bases in length, with an average size of 1000 bases. The DNA was diluted to 0.25 ng/μL in 10 mM TrisHCl, 1 mM EDTA (pH 8.0) and stored at −20° C.

cDNA libraries were prepared using the Lambda-ZAP cDNA cloning kit (Stratagene). From 5 μg of polyA⁺ RNA, approximately $10^6$ clones were recovered per preparation, with an average size of 1 kb and a size range of 500 bp to 3 kb. A hybridization probe for the Populus FLO/LFY homolog was obtained by touchdown PCR (Don et al., 1991) of the cDNA library with a degenerate primer specific to a highly conserved region of the FLO and LFY genes and a primer specific for the vector plus 3'-end of polyadenylated cDNAs. The PCR protocol was as follows: (94° C., 30 sec; 60° C., 30 sec; 71° C., 1 min)×2, (94° C., 30 sec; 58° C., 30 sec; 71° C., 1 min)×2, (94° C., 30 sec; 56° C., 30 sec; 71° C., 1 min)×2, (94° C., 30 sec; 54° C., 30 sec; 71° C., 1 min)×2, (94° C., 30 sec; 52° C., 30 sec; 71° C., 1 min)×2, (94° C., 30 sec; 50° C., 30 sec; 71° C., 1 min)×8, (94° C., 30 sec; 52° C., 30 sec; 71° C., 1 min)×25. The approximately 480 bp fragment obtained was gel-purified and subcloned into pBluescript SK(−) for further characterization.

The PTLF genomic clone was isolated by screening the genomic library using probes derived from the PTLF cDNA sequence. Sequencing of the cDNA was performed using the dideoxy-terminator-based Sequenase 2.0 kit (Unites States Biochemical Corp.), according to the methods described by the manufacturer. Most sequencing of the cDNA and subclones of the gene was done using universal primers on nested deletions created with ExoIII (Henikoff, 1984). Gaps were filled in by sequencing from specific primers synthesized at Oregon State University. Sequence analysis was performed using PCGENE (Intelligenetics).

A total of 5,656 bp of the PTLF gene locus was sequenced, including 2,638 bp upstream of the initiation codon and 457 bp downstream of the polyA addition site. This sequence is available on GenBank (http://www.ncbi.nlm.nih.gov/Entrez/nucleotide.html) under accession number U93196 and is shown in Seq. I.D. No. 5. The positions of the two introns found in both FLO and LFY are conserved in PTLF. The longest cDNA obtained (Seq. I.D. No. 6) includes an open reading frame (Seq. I.D. No. 7) that encodes for a predicted polypeptide of 377 amino acid residues (Seq. I.D. No. 8). Comparison of the deduced PTLF amino acid sequence with several FLO/LFY homologs revealed conserved amino- and carboxyl-terminal domains (133 and 175 residues, respectively, in PTLF) linked by a poorly conserved, highly charged domain (69 residues). The overall sequence identity between PTLF and FLO (Coen et al., 1990) is 79%, with 88% amino acid sequence similarity.

Due to the limited seasonal availability of inflorescence and flower tissue, and the difficulty of obtaining large amounts of developing meristems, the levels of PTLF expression were compared using RT-PCR. PTLF was detected most strongly in developing inflorescences, with no significant differences between samples from male and female trees.

For in situ hybridization analysis, tissue samples from various sources were fixed, embedded, sectioned, and hybridized as described by Kelly et al. (1995), with the following modifications. Sections were 10 μm in thickness. Probes were generated from a plasmid consisting of the PTLF cDNA inserted between the EcoRI and Kpn I sites of the vector pBluescriptII SK (−), and were not alkaline hydrolyzed. A PTLF antisense probe hybridized strongly to the floral meristems and developing flowers of both male and female plants. PTLF was not detected in the apical inflorescence meristem, but was seen in the flanking nascent floral meristems. Developing flowers showed expression in the immature carpels and anthers. Both male and female flowers exhibited some hybridization on the inner (adaxial) rim of the perianth cup during the middle stages of development. PTLF also showed marked hybridization to bracts. Hybridization was observed with vegetative buds from mature branches. The pattern of hybridization showed that there was RNA in the axils of the newly formed leaves, but not in the center of the vegetative meristem. There was also significant expression in the tips of the leaf primordia, and in some portions of the surrounding developing leaves.

Overexpression and antisense constructs of PTLF cDNA were produced for analysis in transgenic trees. The insert from the cDNA clone of PTLF was cut out using EcoR I and Kpn I, and the ends were polished with T4 DNA polymerase. The insert was then ligated into the Sma I site of pBI121 (Jefferson et al., 1987). Clones with each orientation were identified by PCR, and the structures of the junction sites near the promoters of both were verified by sequencing of the PCR fragments. Hybrid aspens were used for transformation, in part because of the relative ease of transformation, and in part because of concern that transgenic cottonwoods might interact with native cottonwoods in the vicinity of the experimental site. The *P. tremula×alba* hybrid aspen female clone 717-1B4 and the *P. tremula× tremuloides* hybrid aspen male clone 353-38 were transformed with pDW151 (Weigel and Nilsson, 1995) and the above binary vectors using *Agrobacterium tumefasciens* strain C58 (Leple et al., 1992) with modifications as described by Han et al. (1996).

Although overexpression of LFY in aspens was reported to result in short, bushy plants that flower within a year (Weigel and Nilsson, 1995), no such obvious phenotypes were seen with PTLF. During more than one year of growth in soil in a greenhouse, and an additional year at a field site in Corvallis, Oreg., few differences were noted for any of the transgenics relative to control plants.

IV. Isolation and Characterization of PTD

The PTD cDNA and gene were isolated by probing the Populus cDNA library described above at low stringency using an Eco RI fragment of pCIT2241 (Ma et al., 1991) which contains the MADS box region of AGL1. The PTD cDNA (Seq. I.D. No. 2) comprises an open reading frame (Seq. I.D. No. 3) encoding a 227 amino acid polypeptide (Seq. I.D. No. 4). The PTD gene (Seq. I.D. No. 1) consists of seven exons.

The PTD polypeptide is 81% conserved overall with respect to DEF. PTD has MADS and K domains. The MADS domain extends over amino acids 1–57, while the K-domain extends over amino acids 87–154. The MADS domain is 93% conserved with respect to DEF, whereas the K domain is 85% conserved at the amino acid level.

To determine if the promoter of PTD would confer the floral-specific expression, 1.9 kb of its promotor and 5' untranslated region were fused to a GUS-intron reporter gene, and introduced into Arabidopsis, tobacco and poplar. GUS expression was observed in floral tissues including petals and stamens. This expression pattern is characteristic of a "B function" gene like APETALA3, suggesting that PTD has retained the regulatory motifs (i.e. sequence patterns) that direct it to stamens and petals (though poplar has no true petals). No vegetative GUS expression was observed, except in poplar, where vegetative expression was confined to leaf-like structures subtending induced floral structures.

V. Isolation and Characterization of PTAG-1 and PTAG2

Two cDNAs and their corresponding genes were isolated from Populus using the methodologies described above and a probe derived from the 3' region of the AG cDNA. Denoted PTAG-1 and PTAG-2, these two sequences are the orthologs of AG.

The genomic, cDNA and open reading frame sequences of PTAG-1 are shown in Seq. I.D. Nos. 9, 10 and 11, respectively. The open reading frame encodes a polypeptide of 241 amino acids in length (Seq. I.D. No. 12). The PTAG-1 polypeptide contains both a MADS domain and a K-domain. The MADS domain extends from amino acids 17–72 and the K-domain from amino acids 106–172. The PTAG-1 nucleotide and amino acid sequences are available on GenBank under accession number AF052570.

The genomic, cDNA and open reading frame sequences of PTAG-2 are shown in Seq. I.D. Nos. 13, 14 and 15, respectively. The open reading frame encodes a polypeptide of 238 amino acids in length (Seq. I.D. No. 16). The PTAG-2 polypeptide contains both a MADS domain and a K-domain. The MADS domain extends from amino acids 16–72 and the K-domain from amino acids 106–172. The PTAG-2 nucleotide and amino acid sequences are available on GenBank under accession number AF052571.

Like AG (Yanofsky et al., 1990), both PTAG1 and PTAG2 contain 8 introns at conserved positions. All introns have canonical donor (GT) and acceptor (AG) sites.

At the amino acid level, PTAG-1 and PTAG 2 are 89% identical, and show 72–75% sequence similarity with AG.

Because AG is only expressed in floral tissues and is essential for the development of both male and female reproductive organs, it is ideally suited for use in modifying fertility through genetic engineering approaches. In situ hybridization studies show that the PTAG genes in Populus are expressed in the central zone of both male and female floral meristems, and, as with AG, expression begins before reproductive primordia emerge and continues in developing stamens and carpels. Northern analysis of PTAG gene expression in populus revealed that transcripts are present in immature and mature flowers from both male and female trees. In addition, low levels of PTAG gene expression are present in all vegetative tissues tested. Interestingly, the size of the transcripts from the vegetative tissues are shorter (~150–200 bp) than the floral transcripts. This size difference is not due to alternate intron/exon splicing.

EXAMPLES

The following examples are provided to illustrate the scope of the invention.

Example 1

Preferred Method of Making the Populus Genes and cDNAs

With the provision of the four Populus floral homeotic nucleic acid sequences PTD, PTLF, PTAG-1 and PTAG-2, the polymerase chain reaction (PCR) may now be utilized in a preferred method for producing the cDNAs and genes, as well as derivatives of these sequences. PCR amplification of the sequence may be accomplished either by direct PCR from an appropriate cDNA or genomic library. Alternatively, the cDNAs may be amplified by Reverse-Transcription PCR (RT-PCR) using RNA extracted from Populus cells as a template. Similarly, the gene sequences may be directly amplified using Populus genomic DNA as a template. Methods and conditions for both direct PCR and RT-PCR are known in the art and are described in Innis et al. (1990). Suitable plant cDNA and genomic libraries for direct PCR include Populus libraries made by methods described above. Other tree cDNA and genomic libraries may be used in order to amplify orthologous cDNAs of tree species, such as Pinus and Eucalyptus.

The selection of PCR primers will be made according to the portions of the cDNA or gene that are to be amplified. Primers may be chosen to amplify small segments of the cDNA or gene, or the entire cDNA or genes. Variations in amplification conditions may be required to accommodate primers of differing lengths; such considerations are well known in the art and are discussed in Innis et al. (1990), Sambrook et al. (1989), and Ausubel et al. (1987). By way of example only, the PTD cDNA molecule as shown in Seq. I.D. No. 2 (with the exception of the 5' poly-A tail) may be amplified using the following combination of primers:

5' ATGGGTCGTGGAAAGATTGAAATCAAG 3' (Seq. I.D. No. 17)

5' ATTTGTGAAAAAGAGCTTTTATATTTA 3' (Seq. I.D. No. 18)

The open reading frame portion of the PTD cDNA may be amplified using the following primer pair:

5' ATGGGTCGTGGAAAGATTGAAATCAAG 3' (Seq. I.D. No. 17)

5' AGGAAGGCGAAGTTCATGGGATCCAAA 3' (Seq. I.D. No. 19)

A derivative version of the PTD ORF that lacks the MADS box domain may be amplified using the following primers:

5' TCCACATCGACAAAGAAGATCTACGAT 3' (Seq. I.D. No. 20)

5' AGGAAGGCGAAGTTCATGGGATCCAAA 3' (Seq. I.D. No. 19)

These primers are illustrative only; it will be appreciated by one skilled in the art that many different primers may be derived from the provided cDNA and gene sequences in order to amplify particular regions of the provided nucleic acid molecules. Suitable amplification conditions include those described above for the original isolation of the PTLF cDNA. As is well known in the art, amplification conditions may need be varied in order to amplify orthologous genes where the sequence identity is not 100%; in such cases, the use of nested primers, as described above may be beneficial. Resequencing of PCR products obtained by these amplification procedures is recommended; this will facilitate confirmation of the amplified cDNA sequence and will also provide information on natural variation on this sequence in different ecotypes, cultivars and plant populations.

Oligonucleotides that are derived from the PTD, PTLF, PTAG-1 and PTAG-2 cDNA and gene sequences and which are suitable for use as PCR primers to amplify corresponding nucleic acid sequences are encompassed within the scope of the present invention. Preferably, such oligonucleotide primers will comprise a sequence of 15–20 consecutive nucleotides of the selected cDNA or gene sequence. To enhance amplification specificity, primers comprising at least 25, 30, 35, 50 or 100 consecutive nucleotides of the PTD, PTLF, PTAG-1 or PTAG-2 gene or cDNA sequences may be used.

Example 2

Use of the Populus Genes and cDNAs to Modify Fertility Characteristics

Once a nucleic acid encoding a protein involved in the determination of a particular plant characteristic, such as flowering, has been isolated, standard techniques may be used to express the nucleic acid in transgenic plants in order to modify that particular plant characteristic. One approach is to clone the nucleic acid into a vector, such that it is operably linked to control sequences (e.g., a promoter)

which direct expression of the nucleic acid in plant cells. The transformation vector is then introduced into plant cells by one of a number of techniques (e.g., electroporation and Agrobacterium-mediated transformation) and progeny plants containing the introduced nucleic acid are selected. Preferably all or part of the transformation vector will stably integrate into the genome of the plant cell. That part of the vector which integrates into the plant cell and which contains the introduced nucleic acid and associated sequences for controlling expression (the introduced "transgene") may be referred to as the recombinant expression cassette.

Selection of progeny plants containing the introduced transgene may be made based upon the detection of an altered phenotype. Such a phenotype may result directly from the nucleic acid cloned into the transformation vector or may be manifested as enhanced resistance to a chemical agent (such as an antibiotic) as a result of the inclusion of a dominant selectable marker gene incorporated into the transformation vector.

The choice of (a) control sequences and (b) how the nucleic acid (or selected portions of the nucleic acid) are arranged in the transformation vector relative to the control sequences determine, in part, how the plant characteristic affected by the introduced nucleic acid is modified. For example, the control sequences may be tissue specific, such that the nucleic acid is only expressed in particular tissues of the plant (e.g., reproductive tissues) and so the affected characteristic will be modified only in those tissues. The nucleic acid sequence may be arranged relative to the control sequence such that the nucleic acid transcript is expressed normally, or in an antisense orientation. Expression of an antisense RNA that is the reverse complement of the cloned nucleic acid will result in a reduction of the targeted gene product (the targeted gene product being the protein encoded by the plant gene from which the introduced nucleic acid was derived). Over-expression of the introduced nucleic acid, resulting from a plus-sense orientation of the nucleic acid relative to the control sequences in the vector, may lead to an increase in the level of the gene product, or may result in a reduction in the level of the gene product due to co-suppression (also termed "sense suppression") of that gene product. In another approach, the nucleic acid sequence may be modified such that certain domains of the encoded peptide are deleted. Depending on the domain deleted, such modified nucleic acid may act as dominant negative mutations, suppressing the phenotypic effects of the corresponding endogenous gene.

Successful examples of the modification of plant characteristics by transformation with cloned nucleic acid sequences are replete in the technical and scientific literature. Selected examples, which serve to illustrate the level of knowledge in this field of technology include:

U.S. Pat. No. 5,432,068 to Albertson (control of male fertility using externally inducible promoter sequences);

U.S. Pat. No. 5,686,649 to Chua (suppression of plant gene expression using processing-defective RNA constructs);

U.S. Pat. No. 5,659,124 to Crossland (transgenic male sterile plants);

U.S. Pat. No. 5,451,514 to Boudet (modification of lignin synthesis using antisense RNA and co-suppression);

U.S. Pat. No. 5,443,974 to Hitz (modification of saturated and unsaturated fatty acid levels using antisense RNA and co-suppression);

U.S. Pat. No. 5,530,192 to Murase (modification of amino acid and fatty acid composition using antisense RNA);

U.S. Pat. No. 5,455,167 to Voelker (modification of medium chain fatty acids)

U.S. Pat. No. 5,231,020 to Jorgensen (modification of flavonoids using co-suppression);

U.S. Pat. No. 5,583,021 to Dougherty (modification of virus resistance by expression of plus-sense RNA); and Mizukami et al. (1996) (dominant negative mutations in floral development using partial deletions of AG).

These examples include descriptions of transformation vector selection, transformation techniques and the production of constructs designed to over-express an introduced nucleic acid, dominant negative mutant forms, untranslatable RNA forms or antisense RNA. In light of the foregoing and the provision herein of the PTD, PTLF, PTAG-1 and PTAG-2 cDNA and gene sequences, it is apparent that one of skill in the art will be able to introduce these cDNAs or genes, or derivative forms of these sequences (e.g., antisense forms), into plants in order to produce plants having modified fertility characteristics, particularly sterility. This Example provides a description of the approaches that may be used to achieve this goal. For convenience the PTD, PTLF, PTAG-1 and PTAG-2 cDNAs and genes disclosed herein will be generically referred to as the "floral homeotic nucleic acids," and the encoded polypeptides as the "floral homeotic polypeptides". Example 3 provides an exemplary illustration of how an antisense form of one of these floral homeotic nucleic acids, specifically the PTD cDNA, may be introduced into poplar species using Agrobacterium transformation, in order to produce genetically engineered sterile poplars. Example 4 provides an exemplary illustration of how mutant forms of PTAG-1 may be produced and introduced into poplar species to produce modified fertility characteristics.

a. Plant Types

The floral homeotic nucleic acids disclosed herein may be used to produce transgenic plants having modified fertility characteristics. In particular, the amenable plant species include, but are not limited to, members of the genus Populus, including *Populus trichocapra* (commonly known as black cottonwood, California poplar and western balsam poplar) and poplar hybrid species. Other woody species that are amenable to fertility modification by the methods disclosed herein include members of the genera Picea, Pinus Pseudotsuga, Tsuga, Sequoia, Abies, Thuja, Libocedrus, Chamaecyparis and Larix. In particular, members of the genera Eucalyptus, Acacia and Gmelina, which are becoming increasingly important for pulp production, may be engineered for sterility using the nucleic acid sequences and methods disclosed here.

b. Vector construction, choice of promoters

A number of recombinant vectors suitable for stable transfection of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences and a dominant selectable marker. Such plant transformation vectors typically also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and/or a polyadenylation signal.

Examples of constitutive plant promoters which may be useful for expressing the floral homeotic nucleic acids include: the cauliflower mosaic virus (CaMV) 35S promoter, which confers constitutive, high-level expression in most plant tissues (see, e.g., Odell et al., 1994, Dekeyser et al., 1990, Terada and Shimamoto, 1990; Benfey and Chua, 1990); the nopaline synthase promoter (An et al., 1988); and the octopine synthase promoter (Fromm et al., 1989).

A variety of plant gene promoters that are regulated in response to environmental, hormonal, chemical, and/or developmental signals, also can be used for expression of the floral homeotic nucleic acids in plant cells, including promoters regulated by: (a) heat (Callis et al., 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991; (c) hormones, such as abscisic acid (Marcotte et al., 1989); (d) wounding (e.g., wunI, Siebertz et al., 1989); and (e) chemicals such as methyl jasminate or salicylic acid (see also Gatz 1997) can also be used to regulate gene expression.

Alternatively, tissue specific (root, leaf, flower, and seed for example) promoters (Carpenter et al., 1992; Denis et al., 1993; Opperman et al., 1993; Stockhause et al., 1997; Roshal et al., 1987; Schermthaner et al., 1988; and Bustos et al., 1989) can be fused to the coding sequence to obtained particular expression in respective organs. In addition, the timing of the expression can be controlled by using promoters such as those acting at senescencing (Gan and Amasino 1995) or late seed development (Odell et al., 1994).

The promoter regions of the PTD, PTLF, PTAG-1 or PTAG-2 gene sequences confer floral-specific (or floral-enriched) expression in Populus. Accordingly, these native promoters may be used to obtain floral-specific (or floral-enriched) expression of the introduced transgene.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

c. Arrangement of floral homeotic nucleic acid sequence in vector

Modified fertility characteristics in plants may be obtained using the floral homeotic nucleic acid sequences disclosed herein in a variety of forms. Over-expression, sense-suppression, antisense RNA and dominant negative mutant forms of the disclosed floral homeotic nucleic acid sequences may be constructed in order to modulate or supplement the expression of the corresponding endogenous floral homeotic genes, and thereby to produce plants having modified fertility characteristics. Alternatively, the floral-specific (or floral-enriched) expression conferred by the promoters of the disclosed floral homeotic genes may be employed to obtain corresponding expression of cytotoxic products. Such constructs will comprise the appropriate floral homeotic promoter sequence operably linked to a suitable open reading frame (discussed further below) and will be useful in genetic ablation approaches to engineering sterility in plants.

i. Modulation/supplementation of Floral Homeotic Nucleic Acid Expression

The particular arrangement of the floral homeotic nucleic acid sequence in the transformation vector will be selected according to the type of expression of the sequence that is desired.

Enhanced expression of a floral homeotic nucleic acid may be achieved by operably linking the floral homeotic nucleic acid to a constitutive high-level promoter such as the CaMV 35S promoter. As noted below, modified activity of a floral homeotic polypeptide in planta may also be achieved by introducing into a plant a transformation vector containing a variant form of a floral homeotic nucleic acid, for example a form which varies from the exact nucleotide sequence of the disclosed floral homeotic nucleic acid.

A reduction in the activity of a floral homeotic polypeptide in the transgenic plant may be obtained by introducing into plants antisense constructs based on the floral homeotic nucleic acid sequence. For expression of antisense RNA, the floral homeotic nucleic acid is arranged in reverse orientation relative to the promoter sequence in the transformation vector. The introduced sequence need not be the full length floral homeotic nucleic acid, and need not be exactly homologous to the floral homeotic nucleic acid found in the plant type to be transformed. Generally, however, where the introduced sequence is of shorter length, a higher degree of homology to the native floral homeotic nucleic acid sequence will be needed for effective antisense suppression. Preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous floral homeotic gene in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous floral homeotic polypeptide activity can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Constructs in which the floral homeotic nucleic acid (or variants thereon) are over-expressed may also be used to obtain co-suppression of the endogenous floral homeotic nucleic acid gene in the manner described in U.S. Pat. No. 5,231,021 to Jorgensen. Such co-suppression (also termed sense suppression) does not require that the entire floral homeotic nucleic acid cDNA or gene be introduced into the plant cells, nor does it require that the introduced sequence be exactly identical to the endogenous floral homeotic nucleic acid gene. However, as with antisense suppression, the suppressive efficiency will be enhanced as (1) the introduced sequence is lengthened and (2) the sequence similarity between the introduced sequence and the endogenous floral homeotic nucleic acid gene is increased.

Constructs expressing an untranslatable form of the floral homeotic nucleic acid mRNA may also be used to suppress the expression of endogenous floral homeotic genes. Methods for producing such constructs are described in U.S. Pat. No. 5,583,021 to Dougherty et al. Preferably, such constructs are made by introducing a premature stop codon into the floral homeotic nucleic acid ORF.

Finally, dominant negative mutant forms of the disclosed sequences may be used to block endogenous floral homeotic polypeptide activity using approaches similar to that described by Mizukami et al. (1996). Such mutants require the production of mutated forms of the floral homeotic polypeptide that bind either to an endogenous binding target (for example, a nucleic acid sequence in the case of floral homeotic polypeptides, such as PTD, that function as transcription factors) or to a second polypeptide sequence (such as transcription co-factors), but do not function normally after such binding (i.e. do not function in the same manner as the non-mutated form of the polypeptide). By way of example, such dominant mutants can be constructed by deleting all or part of the C-terminal domain of a floral homeotic polypeptide, leaving an intact MADS domain. Polypeptides lacking all or part of the C-terminal region may bind to the appropriate DNA target, but are unable to interact with protein co-factors, thereby blocking transcription. Alternatively, dominant negative mutants may be produced by deleting all or part of the MADS domain, or all or part of the K-domain.

ii. Genetic Ablation

An alternative approach to modulating floral development is to specifically target a cytotoxic gene product to the floral tissues. This may be achieved by producing transgenic plants that express a cytotoxic gene product under the control of a floral-specific promoter, such as the promoter regions of PTLF, PTD, PTAG-1 and PTAG-2 as disclosed herein. The promoter regions of these gene sequences are generally contained within the first 150 base pairs of sequence upstream of the open reading frame, although floral-specific expression may be conferred by using smaller regions of this sequence. Thus, regions as small as the first 50 base pairs of sequence upstream of the open reading frame may be effective in conferring floral-specific expression. However, longer regions, such as at least 100, 150, 200 or 250 base pairs of the upstream sequences are preferred.

A number of known cytotoxic gene products may be expressed under the control of the disclosed promoter sequences of the floral homeotic genes. These include: RNases, such as barnase from *Bacillus amyloliquefaciens* and RNase-T1 from Aspergillus (Mariani et al., 1990; Mariani et al., 1992; Reynaerts et al., 1993); ADP-ribosyl-transferase (Diphtheria toxin A chain) (Pappenheimer, 1977; Thorness et al., 1991; Kandasamy et al., 1993); RolC from *Agrobacterium rhizogenes* (Schmulling et al., 1993); DTA (diphtheria toxin A) (Pappenheimer, 1977) and glucanase (Worrall et al., 1992).

d. Transformation and regeneration techniques

Constructs designed as discussed above to modulate or supplement expression of native floral homeotic genes in plants, or to express cytotoxins in a tissue-specific manner can be introduced into plants by a variety of means. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene mediated transformation; transformation using viruses; micro-injection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section.

Methods that are particularly suited to the transformation of woody species include (for Picea species) methods described in Ellis et al. (1991, 1993) and (for Populus species) the use of *A. tumefaciens* (Settler, 1993; Strauss et al., 1995a,b), *A. rhizogenes* (Han et al., 1996) and biolistics (McCown et al., 1991).

e. Selection of transformed plants

Following transformation and regeneration of plants with the transformation vector, transformed plants are preferably selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, the effect on fertility can be determined by visual inspection of floral morphology, including the determination of the production of pollen or ova. In addition, the effect on the activity of the endogenous floral homeotic gene may be directly determined by nucleic acid analysis (hybridization or PCR methodologies) or immunoassay of the expressed protein. Antisense or sense suppression of the endogenous floral homeotic gene may be detected by analyzing mRNA expression on Northern blots or by reverse transcription polymerase chain reaction (RT-PCR).

Example 3

Introduction of Antisense PTD cDNA into Hybrid Aspens

By way of example, the following methodology may be used to produce poplar trees with modified expression of PTD. The PTD cDNA (Seq. I.D. No. 2) is excised from the cloning vector and blunt ended using T4 DNA polymerase. The cDNA is then ligated into the Sma I site of pBI121 (Jefferson et al., 1987), and clones containing the cDNA in reverse orientation with respect to the promoter are identified by sequence analysis.

Hybrid aspens, such as the *P. tremula×alba* hybrid aspen and the *P. tremula×tremuloides* hybrid aspen are transformed with pDW151 (Weigel and Nilsson, 1995) and the above binary vectors using *Agrobacterium tumefasciens* strain C58 (Leple et al., 1992) with modifications as described by Han et al. (1996).

Expression of the antisense transgene is assessed in immature plants by extraction of mRNA and northern blotting using the PTD cDNA as a probe, or by RT-PCR. Levels of PTD protein are analyzed by extraction and concentration of cellular proteins followed by western blotting, or by in situ hybridization.

Example 4

Expression of Mutant PTAG-1 Sequences in Plants

PTAG-1 mutants are constructed by PCR amplification using standard PCR methodologies as described above and a Populus cDNA library as a template. A mutant form of PTAG-1 in which the MADS box domain is deleted is amplified using the following primer combination:
5' GTCACTTTCTGCAAAAGGCGCAGTGGT 3' (Seq. I.D. No. 21)
5' AACTAACTGAAGGGCCATCTGATCTTG 3' (Seq. I.D. No. 22)

A mutant form of PTAG-1 in which a portion of the 3' region of the encoded polypeptide is deleted is amplified using the following primer combination:
5' ATGGAATATCAAAATGAATCCCTTGAG 3' (Seq. I.D. No. 23)
5' ATTCATGCTCTGTCGCTTTCTTTCATTCT 3' (Seq. I.D. No. 24)

The amplified products are cloned using standard cloning vectors and then ligated into a transformation vector such as pBI121 (Jefferson et al., 1987).

Hybrid aspens, such as the *P. tremula×alba* hybrid aspen and the *P. tremula×tremuloides* hybrid aspen are transformed with pDW151 (Weigel and Nilsson, 1995) and the pBI121 binary vector containing the mutant PTAG-1 construct using *Agrobacterium tumefasciens* strain C58 (Leple et al., 1992) with modifications as described by Han et al. (1996).

Expression of the mutant PTAG-1 transgenes is assessed in immature plants by extraction of mRNA and northern blotting using the PTAG-1 cDNA as a probe or by RT-PCR. Levels of mutant protein are analyzed by extraction and concentration of cellular proteins followed by western blotting, or by in situ hybridization.

Example 5

Production of Sequence Variants

As noted above, modification of the activity of floral homeotic polypeptides such as PTD, PTLF, PTAG-1 and PTAG-2 in plant cells can be achieved by transforming plants with a selected floral homeotic nucleic acid (cDNA or gene, or parts therof), antisense constructs based on the disclosed floral homeotic nucleic acid sequences or other variants on the disclosed sequences. Sequence variants include not only genetically engineered sequence variants, but also naturally occurring variants that arise within Populus populations, including allelic variants and polymorphisms, as well as variants that occur in different genotypes and species of Populus. These naturally occurring variants may be obtained by PCR amplification from genomic or cDNA libraries made from genetic material of Populus species, or by RT-PCR from mRNA from such species, or by other methods known in the art, including using the disclosed nucleic acids as probes to hybridize with genetic libraries. Methods and conditions for both direct PCR and RT-PCR are known in the art and are described in Innis et al. (1990).

As noted, variant DNA molecules also include those created by DNA genetic engineering techniques, for example, M13 primer mutagenesis. Details of these techniques are provided in Sambrook et al. (1989), Ch. 15. By the use of such techniques, variants may be created which differ in minor ways from the floral homeotic cDNA or gene sequences disclosed. DNA molecules and nucleotide sequences which are derived from the floral homeotic nucleic acids disclosed include DNA sequences which hybridize under stringent conditions to the DNA sequences disclosed, or fragments thereof.

Nucleic acid molecules and proteins that are variants of those disclosed herein may be identified by the degree of sequence identity that they share with a nucleic acid molecule or protein disclosed herein. Typically, such variants share at least 50% sequence identity with a disclosed nucleic acid or protein, as determined by the methods described above for homologs. Alternatively, for nucleic acid molecules, variants may be identified by their ability to hybridize to a disclosed sequence under stringent conditions, as described above.

The degeneracy of the genetic code further widens the scope of the present invention as it enables major variations in the nucleotide sequence of a DNA molecule while maintaining the amino acid sequence of the encoded protein. For example, the 32nd amino acid residue of the Poplar PTD protein shown in Seq. I.D. No. 4 is alanine. This is encoded in the Poplar PTD open reading frame by the nucleotide codon triplet GCC. Because of the degeneracy of the genetic code, three other nucleotide codon triplets: GCT, GCA and GCG, also code for alanine. Thus, the nucleotide sequence of the Poplar PTD ORF could be changed at this position to any of these three codons without affecting the amino acid composition of the encoded protein or the characteristics of the protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences which encode a floral homeotic protein but which vary from the disclosed nucleic acid sequences by virtue of the degeneracy of the genetic code.

One skilled in the art will recognize that DNA mutagenesis techniques may be used not only to produce variant DNA molecules, but will also facilitate the production of proteins which differ in certain structural aspects from the Poplar floral homeotic proteins, yet which proteins are clearly derivative of these proteins. Newly derived proteins may also be selected in order to obtain variations on the characteristic of the Poplar floral homeotic proteins. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of two residues or insertion of two residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure.

Substitutional variants are those in which at least one residue in the amino acid sequence has been removed and a different residue inserted in its place. Such substitutions generally are made in accordance with the following Table 1 when it is desired to finely modulate the characteristics of the protein. Table 1 shows amino acids which may be substituted for an original amino acid in a protein and which are typically regarded as conservative substitutions.

TABLE 1

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in transcription factor function or other features are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Homologous polypeptides that share at least 50% amino acid sequence identity to the disclosed PTD, PTLF, PTAG-1 or PTAG-2 amino acid sequences as determined using BLAST 2.0, gapped blastp, with default parameters, are encompassed by this invention. Homologs with even greater similarity to the reference sequences will show increasing percentage identities when assessed by this method, such as at least 60%, at least 65%, at least 70%, at least 75%, at least 80%, at least 90% or at least 95% sequence identity. Such homologous peptides are preferably at least 10 amino acids in length, and more preferably at least 25 or 50 amino acids in length. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Also encompassed by the present invention are the nucleic acid sequences that encode these homologous peptides.

Similarly, homologous nucleic acids that share at least 50% nucleotide identity to the disclosed PTD, PTLF, PTAG-1 or PTAG-2 nucleic acid sequences as determined using BLAST 2.0, gapped blastn, with default parameters, are encompassed by this invention. Homologs with even greater similarity to the reference sequences will show increasing percentage identities when assessed by this method, such as at least 60%, at least 65%, at least 70%, at least 75%, at least 80%, at least 90% or at least 95% sequence identity. Such homologous nucleic acids are preferably at least 50 nucleotides on length, and more preferably at least 100 or 250 nucleotides in length.

Example 6

Other Applications of the Disclosed Sequences

The disclosed floral homeotic nucleic acids and polypeptide are useful as laboratory reagents to study and analyze floral gene expression in plants, including plants engineered for modified fertility characteristics. For example, probes and primers derived from the PTD sequence, as well as monoclonal antibodies specific for the PTD polypeptide may be used to detect and quantify expression of PTD in seedlings transformed with an antisense PTD construct as described above. Such analyses would facilitate detection of those transformants that display modified PTD expression and which may therefore be good candidates for having modified fertility characteristics.

The production of probes and primers derived from the disclosed sequences is described in detail above. Production of monoclonal antibodies requires that all or part of the protein against which the antibodies to be raised be purified. With the provision herein of the floral homeotic nucleic acid sequences, as well as the sequences of the encoded polypeptides, this may be achieved by expression in heterologous expression systems, or chemical synthesis of peptide fragments.

Many different expression systems are available for expressing cloned nucleic acid molecules. Examples of prokaryotic and eukaryotic expression systems that are routinely used in laboratories are described in Chapters 16–17 of Sambrook et al. (1989). Such systems maybe used to express the floral homeotic polypeptides at high levels to faciliate purification.

By way of example only, high level expression of a floral homeotic polypeptide may be achieved by cloning and expressing the selected cDNA in yeast cells using the pYES2 yeast expression vector (Invitrogen, San Diego, Calif.). Secretion of the recombinant floral homeotic polypeptide from the yeast cells may be achieved by placing a yeast signal sequence adjacent to the floral homeotic nucleic acid coding region. A number of yeast signal sequences have been characterized, including the signal sequence for yeast invertase. This sequence has been successfully used to direct the secretion of heterologous proteins from yeast cells, including such proteins as human interferon (Chang et al., 1986), human lactoferrin (Liang and Richardson, 1993) and prochymosin (Smith et al., 1985). Alternatively, the enzyme may be expressed at high level in prokaryotic expression systems, such as *E. coli*.

Monoclonal or polyclonal antibodies may be produced to the selected floral homeotic polypeptide or portions thereof. Optimally, antibodies raised against a specified floral homeotic polypeptide will specifically detect that polypeptide. That is, for example, antibodies raised against the PTD polypeptide would recognize and bind the PTD polypeptide and would not substantially recognize or bind to other proteins found in poplar cells. The determination that an antibody specifically detects PTD is made by any one of a number of standard immunoassay methods; for instance, the Western blotting technique (Sambrook et al., 1989). To determine that a given antibody preparation (such as one produced in a mouse against PTD) specifically detects PTD by Western blotting, total cellular protein is extracted from poplar cells and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect PTD will, by this technique, be shown to bind to substantially only the PTD band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-PTD binding.

Substantially pure floral homeotic polypeptides suitable for use as an immunogen may be isolated from transformed cells as described above. Concentration of protein in the fmal preparation is adjusted, for example, by concentration on an Amicon filter device, to the level of a few micrograms per milliliter. Alternatively, peptide fragments of the specified floral homeotic polypeptide may be utilized as immunogens. Such fragments may be chemically synthesized using standard methods, or may be obtained by cleavage of the whole floral homeotic polypeptide followed by purification of the desired peptide fragments. Peptides as short as 3 or 4 amino acids in length are immunogenic when presented to the immune system in the context of a Major Histocompatibility Complex (MHC) molecule, such as MHC class I or MHC class II. Accordingly, peptides comprising at least 3 and preferably at least 4, 5, 6 or 10 or more consecutive amino acids of the disclosed floral homeotic polypeptide amino acid sequences may be employed as inumuogens to raise antibodies. Because naturally occurring epitopes on proteins are frequently comprised of amino acid residues that are not adjacently arranged in the peptide when the peptide sequence is viewed as a linear molecule, it may be advantageous to utilize longer peptide fragments from the floral homeotic polypeptide amino acid sequences in order to raise antibodies. Thus, for example, peptides that comprise at least 10, 15, 20, 25 or 30 consecutive amino acid residues of the floral homeotic polypeptide amino acid sequence may be employed. Monoclonal or polyclonal antibodies to the intact floral homeotic polypeptide or peptide fragments of this protein may be prepared as described below.

Monoclonal antibody to epitopes of the selected floral homeotic polypeptide can be prepared from murine hybridomas according to the classical method of Kohler and Milstein (1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988).

Having illustrated and described the principles of isolating the Populus floral homeotic genes, the proteins encoded by these genes and modes of use of these biological molecules, it should be apparent to one skilled in the art that the invention can be modified in arrangement and detail without departing from such principles. We claim all modifications coming within the spirit and scope of the claims presented herein.

REFERENCES

Ainley et al. (1993). Regulatable endogenous production of cytokinins up o "toxic" levels in transgenic plants and plant tissues. *Plant Mol. Biol.* 22:13–23.

Altschul et al. (1990). *J. Mol. Biol.* 215:403–410.

Altschul et al. (1994). *Nature Genetics* 6:119–129.

An et al. (1988). *Plant Physiol.* 88: 547.

Ausubel et al. (1987). In: Current Protocals in Molecular Biology, Greene Publishing Associates and Wiley-lntersciences.

Baker et al. (1990). RNA and DNA isolation from recalcitrant plant tissues. *Bio/Techniques* 9:268–272.

Benfey and Chua (1990). The cauliflower mosaic virus 35S promoter: Combinatorial regulation of transcription in plants. *Science* 250:959–966.

Boes and Strauss (1994). Floral phenology and morphology of black cottonwood, *Populus trichocapra* (Salicaceae). *Am. J. Bot.* 8:562–567.

Brayshaw (1965). The status of the black cottonwood (*Populus trichocarpa* Torreyand Gray). *Can. Field Nat.* 79:91–95.

Brusslan et al. (1993). An Arabidopsis mutant with a reduced level of cab140 RNA is aresult of cosuppression. *Plant Cell* 5:667–677.

Bustos et al. (1989). *Plant Cell* 1: 839.

Callis et al. (1988). *Plant Physiol.* 88: 965.

Carpenter et al. (1992). Preferential expression of an α-tubulin gene of Arabidopsis in pollen. *Plant Cell* 4:557–571.

Chang et al. (1986). *Saccharomyces cerevisiae* secretes and correctly processes human interferon hybrid protein containing yeast invertase signal peptides. *Mol. and Cell. Biol.* 6:1812–1819.

Cheng et al. (1983). Organ initiation and the development of unisexual flowers in the tassel and ear of *Zea mays. Am. J. Bot.* 70:450–462.

Coen et al. (1990). FLORICAULA: a homeotic gene required for flower development in *Antirrhinum majus. Cell* 63:1311–1322.

Corpet et al. (1988). *Nucleic Acids Research* 16:10881–10890.

Dekeyser et al. (1990). *Plant Cell* 2:591.

Denis et al. (1993). Expression of engineered nuclear male sterility in *Brassica napus. Plant Physiol.* 101: 1295–1304.

Don et al. (1991). "Touchdown" PCR to circumvent spurious priming during gene amplification. *Nucl. Acids Res.* 19:4008.

Ellis et al. (1991). *Plant. Mol. Biol.* 17:19–27.

Ellis et al. (1993). *Bio/Technology* 11:84–89.

Engvall (1980). *Enzymol.* 70:419.

Flavell (1994). Inactivation of gene expression in plants as a consequence of specific sequence duplication. *Proc Natl Acad Sci USA* 91:3490–3496.

Fromm et al. (1989). *Plant Cell* 1:977.

Gan and Amasino (1995). Inhibition of leaf senescence by autoregulated production of cytokinin. *Science* 270:1986–1988.

Gatz (1997). Chemical control of gene expression. *Ann. Rev. Plant Physiol. Plant Mol. Biol.* 48:89–108.

Gelvin et al. (1990). Plant Molecular Biology Manual, Kluwer Academic Publishers.

Gilmartin et al. (1992). Characterization of a gene encoding a DNA binding protein with specificity for a light-responsive element. *Plant Cell* 4:839–949.

Goldman et al. (1994). Female sterile tobacco plants are produced by stigma-specific cell ablation. *EMBO J.* 13:2976–2984.

Grant et al. (1994). Developmental differences between male and female flowers in the dioecious plant *Silene latifolia*. *Plant J.* 6:471–480.

Han et al. (1996). Cellular and molecular biology of Agrobacterium-mediated transformation of plants and its application to genetic transfonnation of Populus. In: Stettler et al. [eds.] Biology of Populus and its Implications for Management and Conservation, Part I, Chapter 9, pp. 201–222, NRC Research Press, Nat. Res. Coun. of Canada, Ottawa, Ontario.

Harlow and Lane (1988). Antibodies: A Laboratory Manual, Cold Spring Harbor Laboratory, New York.

Henikoff (1984). Unidirectional digestion with exonuclease III creates targeted breakpoints for DNA sequencing. *Gene* 28:351–359.

Higgins and Sharp (1988). *Gene* 73: 237–244.

Higgins and Sharp (1989). *CABIOS* 5:151–153.

Huang et al. (1992). *Computer Applications in the Biosciences* 8:155–165.

Innis et al. (1990). PCR Protocols, A Guide to Methods and Applications, Innis et al. [eds.], Academic Press, Inc., San Diego, Calif.

Jefferson et al. (1987). GUS fusions: β-glucuronidase as a sensitive and versatile gene fusion marker in higher plants. *EMBO J.* 6:3901–3907.

Jorgensen (1992). Silencing of plant genes by homologous transgenes. *AgBiotech News Info* 4:265N–273N.

Kandasamy et al. (1993). Ablation of papillar cell finction in Brassica flowers results in the loss of stigma receptivity to pollination. *Plant Cell* 5:263–275.

Kaul (1995). Reproductive structure and organogenesis in a cottonwood, *Populus deltoides* (Salicaceae). *Int. J. Plant Sci.* 156:172–180.

Kawasaki et al. (1990). In: PCR Protocals, A Guide to Methods and Applications, Innis et al. [eds.], pp. 21–27, Academic Press, Inc., San Diego, Calif.

Kelly et al. (1995) NFL, the tobacco homolog of FLORICAULA and LEAFY, is transcriptionally expressed in both vegetative and floral meristems. *Plant Cell* 7:225–34.

Kohler and Milstein (1975). *Nature* 256:495.

Kooter (1993). Mol JNM: Trans-inactivation of gene expression of plants. *Curr Opin Biotechnol* 4:166–171.

Kuhlemeier et al. (1989). *Plant Cell* 1:471.

Leple et al. (1992). Transgenic poplars: Expression of chimeric genes using four different constructs. *Plant Cell Rep.* 11:137–41.

Liang and Richardson (1993). Expression and characterization of human lactoferrin in yeast (*Saccharomyces cerevisiae*). *J. Agric. Food Chem.* 41:1800–1807.

Ma (1994). The unfolding drama of flower development: Recent results from genetic and molecular analyses. *Genes Dev.* 8:745–756.

Ma et al. (1991). AGL1–AGL6, an Arabidopsis gene family with similarity to floral homeotic and transcription factor genes. *Genes & Dev.* 5:484–495.

Mandel et al. (1992a). Manipulation of flower structure in transgenic tobacco. *Cell* 71:133–143.

Mandel et al. (1992b). Molecular characterization of the Arabidopsis floral homeotic gene APETALA1. *Nature* 360: 273–277.

Marcotte et al. (1989). *Plant Cell* 1:969.

Mariani et al. (1990). Induction of male sterility in plants by a chimaeric ribonucleae gene. *Nature* 347:737–741.

Mariani et al. (1992). A chimaeric ribonuclease-inhibitor gene restores fertility to male-sterile plants. *Nature* 357:384–387.

Matzke et al. (1993). Genomic imprinting in plants: parental effects and trans-inactivation phenomena. *Annu. Rev. Plant Physiol. Plant Mol. Biol.* 44:53–76.

McCown et al. (1991). Stable transformation of Populus and incorporation of pest resistance by electric discharge particle acceleration. *Plant Cell Rep.* 9:590–594.

Mizukami et al. (1996). *Plant Cell* 8:831–845

Mol et al. (1994). Post-transcriptional inhibition of gene expression: Sense and antisense genes. In: Paszkowski J (ed.) Homologous Recombination and Gene Silencing in Plants, pp. 309–334, Kluwer Academic Publishers, Dordrecht.

Nagaraj (1952). Floral morphology of *Populus deltoides* and *P. tremuloides*. *Bot. Gaz.* 114:222–243.

Needleman and Wunsch (1970). *J. Mol. Biol.* 48:443.

Odell et al. (1994). Seed specific gene activation mediated by the Cre/lox site-specific recombination system. *Plant Physiol.* 106:447–458.

Okamuro et al. (1993). Regulation of Arabidopsis flower development. *Plant Cell* 5:1183–93.

Opperman et al. (1993). Root knot nematode directed expression of a plant root specific gene. *Science* 263:221–223.

Pappenheimer (1977). Diphtheria toxin. *Annu. Rev. Biochem.* 46:69–94.

Paul et al. (1992). The isolation and characterization o the tapetum-specific *Arabidopsis thaliana* A9 gene. *Plant Mol Biol* 19:611–622.

Pearson and Lipman (1988). *Proc. Natl. Acad. Sci. USA* 85:2444.

Pearson et al. (1994). *Methods in Molecular Biology* 24:307–331.

Pnueli et al. (1991). *Plant J.* 1:255–266.

Pnueli et al. (1994). Isolation of the tomato Agamous gene TAG1 and analysis of its homeotic role in transgenic plants. *Plant Cell* 6:163–173.

Pouwels et al. (1987). Cloning Vectors: A Laboratory Manual, 1985 supplement.

Purugganan et al. (1995). Molecular evolution of flower development: Diversification of the plant MADS-box regulatory gene family. *Genetics* 140:345–56.

Reynaerts et al. (1993). Engineered genes for fertility control and their application in hybrid seed production. *Sci. Hortic* 55:125–139.

Riechmann et al. (1996). DNA binding properties of Arabidopsis MADS domain homeotic proteins APETELA1, APETELA3, PISTILLATA and AGAMOUS. *Nuc. Acid. Res.* 24(16): 3134–3141.

Roshal et al. (1987). *EMBO J.* 6:1155.

Sambrook et al. (1989). Molecular Cloning: A laboratory manual,. Cold Spring Harbor Laboratory, Cold Spring Harbor, N.Y.

Schaffier and Sheen (1991). *Plant Cell* 3:997.

Scheruthaner et al. (1988). *EMBO J.* 7:1249.

Schmulling et al. (1993). Resoration of fertility by anti-sense RNA in genetically engineered male sterile tobacco plants. *Mol. Gen. Genet.*237–385–394.

Schwarz-Sommer et al. (1992). *EMBO J.* 11: 251–263.

Sheppard (1997). PTD: a *Populus trichocapra* gene with homology to floral homeotic transcription factors. Ph.D. dissertation. Oregon State University.

Siebertz et al. (1989). *Plant Cell* 1:961.

Smith and Waterman (1981). *Adv. Appl. Math.* 2:482.

Smith et al. (1985). Heterologous protein secretion from yeast. *Science* 229:1219–1224.

Stettler (1993). Popular Molecular Network Newsletter 1(1), College of Forest Resources AR-10, University of Washington, Seattle, Wash.

Stockhause et al. (1997). The promoter of the gene encoding the $C_4$ Flaveria spp. *Plant Cell* 9:479–489.

Strauss et al. (1995a). *Molecular Breeding* 1:5–26.

Strauss et al. (1995b). TGERC Annual Report: 1994–1995. Forest Research Laboratory, Oregon State University.

Taylor et al. (1992). Conditional male-fertility in chalcone synthase-deficient petunia. *J Hered.* 83:11–17.

Terada and Shimamoto (1990). *Mol. Gen. Genet.* 220:389.

Thorsness et al. (1991). A Brassica S-locus gene promoter targets toxic gene expression and cell death to the pistil and pollen of transgenic Nicotiana. *Devel. Biol.* 143:173–184.

Thorsness et al. (1993). Genetic ablation of floral cells in Arabiodopsis. *Plant Cell* 5:253–61.

Tijssen (1993). Overview of principles of hybridization and the strategy of nucleic acid probe assays. In: Laboratory Techniques in Biochemistry and Molecular Biology -Hybridization with Nucleic Acid Probes, Part I, Chapter 2. Elsevier, N.Y.

Van der Meer et al. (1992). Antisense inhibition of flavanoid biosynthesis sin petunia anthers results in male sterility. *Plant Cell* 4:253–262.

Wagner et al. (1987). Chloroplast DNA polymorphisms in lodgepole pine and their hybrids. *Proc. Natl. Acad. Sci. USA* 84:2097–2100.

Weigel et al. (1992). LEAFY controls floral meristem identity in Arabidopsis. *Cell* 69:843–59.

Weigel and Nilsson (1995). A developmental switch sufficient for flower initiation in diverse plants. *Nature* 377: 495–500.

Weissbach and Weissbach (1989). Methods for Plant Molecular Biology, Academic Press.

Worrall et al. (1992). Premature dissolution of the microporocyte callose wall causes male sterility in transgenic tobacco. *Plant Cell* 4:759–771.

Yanofsky (1995). Floral meristems to floral organs: Genes controlling early events in Arabidopsis flower development. *Annu. Rev. Plant Physiol.* 46:167–188.

Yanofsky et al. (1990). The protein encoded by the Arabidopsis homeotic gene AGAMOUS resembles transcription factors. *Nature* 346: 35–39.

---

We claim:

1. An isolated nucleic acid molecule comprising at least 35 consecutive nucleotides of a nucleic acid sequence shown in SEQ ID NO: 1.

2. An isolated nucleic acid molecule according to claim 1 wherein the nucleic acid molecule includes at least 40 consecutive nucleotides of the specified nucleic acid sequence.

3. An isolated nucleic acid molecule according to claim 1 wherein the nucleic acid molecule includes at least 50 consecutive nucleotides of the specified nucleic acid sequence.

4. An isolated nucleic acid, wherein the nucleic acid is a PTD promoter and hybridizes under wash conditions of 0.2×SSC, 0.1% SDS at 65° C. to a nucleic acid sequence shown as nucleotides 1–1872 of SEQ ID NO: 1.

5. The isolated nucleic acid of claim 4, wherein the PTD promoter is a floral-specific promoter.

6. The isolated nucleic acid of claim 5, wherein the floral-specific promoter confers gene expression predominantly in a floral tissue.

7. The isolated nucleic acid of claim 6, wherein the floral tissue is a stamen.

8. The isolated nucleic acid of claim 6, wherein the floral tissue is a petal.

9. The isolated nucleic acid of claim 4, wherein the nucleic acid that is a PTD promoter and hybridizes under wash conditions of 0.2×SSC, 0.1% SDS at 65° C. to the nucleic acid sequence shown as nucleotides 1–1872 of SEQ ID NO: 1comprises at least 50 consecutive nucleotides of the nucleic acid sequence shown as nucleotides 1–1872 of SEQ ID NO: 1.

10. The isolated nucleic acid of claim 9, wherein the nucleic acid that is a PTD promoter and hybrdizes under wash conditions of 0.2×SSC, 0.1% SDS at 65° C. to the nucleic acid sequence shown as nucleotides 1–1872 of SEQ ID NO: 1 comprises at least 100 consecutive nucleotides of the nucleic acid sequence shown as nucleotides 1–1872 of SEQ ID NO: 1.

11. The isolated nucleic acid of claim 4, wherein te nucleic acid that is a PTD promoter and comprises a nucleotide sequence of at least 35 consecutive nucleotides of nucleotides 1–1872 of SEQ ID NO: 1.

12. The isolated nucleic acid of claim 4, wherein the nucleic acid that is a PTD promoter and comprises a nucleotide sequence of at least 40 consecutive nucleotides of nucleotides 1–1872 of SEQ ID NO: 1.

13. The isolated nucleic acid of claim 4, wherein the nucleic acid that is a promoter and comprises a nucleotide sequence of at least 75 consecutive nucleotides of nucleotides 1–1872 of SEQ ID NO: 1.

14. The isolated nucleic acid of claim 4, wherein the nucleic acid comprises a nucleic acid sequence shown as nucleotides 1–1872 of SEQ ID NO: 1.

15. A recombinant nucleic acid comprising the isolated nucleic acid of claim 14.

16. A transgenic plant comprising the recombinant nucleic acid of claim 15.

17. The recombinant nucleic acid of claim 15 wherein the nucleic acid is operably linked to a first nucleic acid.

18. The recombinant nucleic acid of claim 17, wherein the first nucleic acid is a cytotoxic peptide.

19. A cell transformed with the recombinant nucleic acid of claim 15.

20. A transgenic plant comprising the recombinant nucleic acid of claim 17.

21. The transgenic plant of claim 20, wherein the PTD promoter enhances expression of the first nucleic acid in a floral tissue in the plant relative to a non-floral tissue in the plant.

22. The transgenic plant of claim 20, wherein the plant has a modified phenotype relative to non-transgenic plants of the same species.

23. A transgenic plant according to claim 22, wherein the modified phenotype is a modified fertility phenotype.

24. A transgenic plant according to claim 23, wherein the modified fertility phenotype is sterility.

25. The transgenic plant of claim 20, wherein the plant is a Populus species.

26. The transgenic plant of claim 20, wherein the plant is a Eucalyptus species.

* * * * *

UNITED STATES PATENT AND TRADEMARK OFFICE
CERTIFICATE OF CORRECTION

PATENT NO. : 6,395,892 B1
DATED : May 28, 2002
INVENTOR(S) : Strauss et al.

It is certified that error appears in the above-identified patent and that said Letters Patent is hereby corrected as shown below:

Column 1,
Line 4, the following heading and paragraph should be added:
-- Acknowledgement of Government Support:
Some of the work described in this patent application was funded by (1) EPA Grant No. CR-822880-01; (2) USDA NRI Plant Genetic Mechanisms Grant No. 93-37301-9425; (3) EPA Exploratory Research Grant No. R-817104-02; (4) NSF Grant Nos. BSR-8957023 and EEC-9980423; (5) Martin Marietta Energy Systems/DOE, Grant Nos. 85X-ST807V, 85X-SP655V; (6) Department of Energy/Agenda 2020, Grant No. DE-FC07-97ID13552; and (7) Forest Industries Grant No. Z0019A (TGERC Coop). The government may have certain rights in this invention. --
Line 60, "RoiC" should be -- *RolC* --.
Line 60, "Schmüilling" should be -- Schmülling --.

Column 2,
Line 24, "APETALAI" should be -- APETALA1 --.

Column 3,
Line 48, "alnost" should be -- almost --.

Column 10,
Line 65, "Md." should be -- MD --.

Column 11,
Line 3, "blast hel-p.html" should be -- blast_help.html --.
Lines 21-22, "blast FAQs.html" should be -- blast_FAQs.html --.
Line 31, "fall" should be -- full --.

Column 12,
Line 35, "innis" should be -- Innis --.
Line 45, "DATP" should be -- dATP --.

Column 14,
Line 65, "PTAG2" should be -- PTAG-2 --.

Column 15,
Line 36, "populus" should be -- *Populus* --.

Column 19,
Line 23, "obtained" should be -- obtain --.

UNITED STATES PATENT AND TRADEMARK OFFICE
CERTIFICATE OF CORRECTION

PATENT NO. : 6,395,892 B1
DATED : May 28, 2002
INVENTOR(S) : Strauss et al.

It is certified that error appears in the above-identified patent and that said Letters Patent is hereby corrected as shown below:

<u>Column 27,</u>
Line 26, "fmal" should be -- final --.
Line 38, "pereferably" should be -- preferably --.
Line 41, "inumuogens" should be -- immunogens --.

<u>Column 28,</u>
Line 20, "o" should be -- to --.
Line 38, "Torreyand" should be -- Torrey and --.
Line 41, "aresult" should be -- a result --.

<u>Column 29,</u>
Line 51, "finction" should be -- function --.

<u>Column 30,</u>
Line 54, "o" should be -- of --.

<u>Column 31,</u>
Line 16, "Schaffier" should be -- Schaffner --.
Line 17, "Scheruthaner" should be -- Schernthaner --.
Line 18, "Resoration" should be -- Restoration --.
Line 21, "237-385" should be -- 237: 385 --.

<u>Column 32,</u>
Line 18, "Sin" should be -- in --.

<u>Columns 31-32,</u>
In the Sequence Listing: "<213> ORGANISM: Populus balsamifera subsp. trichoc arpa" should be -- <213> ORGANISM: Populus balsamifera subsp. trichocarpa --.

<u>Column 85,</u>
Line 54, "65° C." should be -- 65°C --.
Line 67, "65° C." should be -- 65°C --.

UNITED STATES PATENT AND TRADEMARK OFFICE
CERTIFICATE OF CORRECTION

PATENT NO. : 6,395,892 B1
DATED : May 28, 2002
INVENTOR(S) : Strauss et al.

It is certified that error appears in the above-identified patent and that said Letters Patent is hereby corrected as shown below:

Column 86,
Line 42, "1comprises" should be -- 1 comprises --.
Line 46, "65° C." should be -- 65°C --.
Line 51, "te" should be -- the --.
Line 67, "claim 14" should be -- claim 4 --.
Line 60, "a promoter" should be -- a PTD promoter --.

Signed and Sealed this

Sixteenth Day of September, 2003

JAMES E. ROGAN
*Director of the United States Patent and Trademark Office*

SEQUENCE LISTING

```
<160> NUMBER OF SEQ ID NOS: 24

<210> SEQ ID NO 1
<211> LENGTH: 4285
<212> TYPE: DNA
<213> ORGANISM: Populus balsamifera subsp. trichoc arpa

<400> SEQUENCE: 1
aagcttgtca gacccaacaa atatggacct gatatgcttg tcataccaac t taaactcga      60 gtcagatata tttaatatta ttattcatat tattaatata attattaata a atttgaaaa     120 aatattatta ctatcgaaaa aaactataaa tttgatttga atgataaaat t aaaaattaa     180 aaatatttt attatcatta ttgttaatat aattattaaa aaatttaaaa a atatattat     240 tactattgag aaaaaccata actgtttatg cgacatttta tgtcatggaa a atgagctga     300 aaaaaccaa taaaagaaa aaaactaatg aaaaaaaaga aaaaaaaata t gaattaact     360 gggttaaccc ttgaaaccag gttacccccgt caaaccttgg attcgtgtcg t gaaagtttg     420 ttaactaaat agaaaaaaaa aattgacggg ttacccagaa ttaactgggc t aacccgtca     480 aaccaggtta cctatcaaac ccgggatccg tgtcatgaaa gtttgataac t aaatagaaa     540
```

```
acaattgaac attaacaacc taaattaaac gaaaaaatt aattaaaaac a agaaaacaa      600
aaacaaacaa aaaacataag catgttagta atgaggaaaa agaaaaaaaa t ttgattcaa      660
ctgagttaac ccgtcaaacc cgggattcgc gtcatgaaag tttgataact a aatagaaaa      720
aaaaatcgac gggttaaacg aaaaaaaatt aacaaactaa actaaacaaa a aaaaattga      780
ttaaaaagga aaaaagcaaa aaaaataatt tcgggttaac tcatcaaacc a ggttaaccc      840
gtcaaacccg agatccgtgt catgaaagtc tgataactaa ataatttttt t tttcacatt      900
aacaaactaa attaaacaaa aaaaattcat taaaagaaaa aaaacacaa a gaaaaaagc      960
aaaaaaaaac ctataatagc ataaataaat aaataaaaac aggaaaaaaa t tttttaaaa     1020
aaaacctttc aatcactaat acatagaagg tgtggggaaa gccacagtga t ttccccgta     1080
cctttttaaag tattacttaa tatataggtg aatttaattg accgtcacga a aaagactat     1140
tctggcttcc tcttacaatg gacgctatct aaattcaaat actttgaaaa a agatttaat     1200
cctgtaacct tctttcgttt tttatgcct tcaatccatc tatttattgt t tttatgatt     1260
tttcttagat acaaaagagc atattttaaa gaagaaaaa ataagctaag c acctcaagt     1320
tttgattttt tttttatttt gcagccaatt ttttaaatat taaaatttc a taatagatc     1380
aaaggataat tcaaaattgc atccaaataa caacattagt aatggaagga c ttatggtat     1440
gaatggatca ataatataag ggctgaatta acaacatttt ttttatttag a tcctgttta     1500
tttttacgtt ttaaaaatat ttttgaaatt attttatttt ttattataaa t taatatttt     1560
tagatcattt taatacgtta atataaaaaa taattttttt aaaaaatt t ttttaatat     1620
attttttaaa aataatattt aaaaaaacaa tcataacaat attctcatta c ctaacacag     1680
tcatggaaca ggaatgagaa aaggtcttat cagtaaattg cttgcatgtc a tgtcaaggt     1740
gtatgaacct cccaatactt ctcacgctac ccttcagaaa tccaatctca g aagccacag     1800
acaatctaag ttacgctaca atcaactttc catcaccctt tccttattta g aaactccac     1860
ttaatcacat ttcacccttt ttcatcatct tctctttccc ttcaagaagc c taggtactg     1920
tgcaagaaac ccttatctct ccccctcagt atttactttt gtttagtgct a cagctttca     1980
caaagaagta aggaaaaaat atgggtcgtg gaaagattga atcaagaag a tcgaaaacc     2040
ccacaaacag gcaagtcacc tactcgaaga gaagaaatgg tattttcaag a aagcccaag     2100
aactcactgt actttgtgat gctaaggtct ctcttatcat gttctccaac a ctaacaaac     2160
tcaatgagta cattagcccc tccacatcgt acgtatactc gtatcatgtt t ctggctaag     2220
tatttcttcc gtgctttctc ttctttcttt ttttcttgt cttttatgtt g cagttttat     2280
gaaaccttgg taatggaacc gtagttttta ttgttaatta tgaccaggac a agaagatc     2340
tacgatcaat atcagaacgc tttaggcata gatctgtggg gcactcaata c gaggttaac     2400
cttttctttc tgtctttctt ctaatgtttg atctatagga cgaatatgag a ttcttcaaa     2460
ggattttgtt tgtgaggttt gcagaaaatg caagagcact tgaggaagct g aatgatatc     2520
aatcataagc tgagacaaga atcaggtaa cttcaaaaga ataaccttc g catatatgc     2580
atgtggttat ggttttatg ggaatatctg taaatttgtg gagctactaa t taaggtatt     2640
tgttttaac aggcagagga gaggagaggg cctgaatgat ctgagcattg a tcatctgcg     2700
cggtcttgag caacatatga ctgaagcctt gaatggtgtg cgtggcagga a ggtcagatg     2760
ttttcaagtg aacatctttta tataattatc aagttctaat tcctaaaatt t gagcttact     2820
agtaatttga gttcggtccg gtgtatcaag caggttaatc tagatctagt t ttttttcct     2880
```

-continued

```
taccaaatca aagtcatttt gaggatttt  taataaaaaa tattgaattt t gaatcaact    2940 tatacaaatt catcaatcta caactcgaat cttacattta atcaaacttt c aaattagat    3000 cttataaata tgatattaac cggtcggtgt tttatgtaca ttaatattat g ttttagttg    3060 aactcttta tcattttttt ttttaaatt  tgagttattt taatccttat c aatttttat    3120 cattttggga ttcttggaaa ccctggttag aaagaaaata cacacccttg a acttgtgct    3180 tctttacctt tgcattatgg attttcatga actggatttt gggtaaccct t aacctcatc    3240 tatagaaggg atatgccttg taattaacac tttacactta caagttcaac a ttctttgat    3300 tatttacagt accatgtgat caaaacacaa aacgaaacct acaggaagaa g gttagtgat    3360 aaaaagaaca ttttacctct tcaatttcat gcatgtagct tttggaacaa a ttctctggc    3420 gattaattgc aggtgaagaa tttagaggag agacatggaa acctcttgat g gaatatgta    3480 agaatctaaa ttttcatgtg cttgttttcg ctaattttcc aacttggaaa a acacatgga    3540 ttaaacctga gatttttttt ttcttttgtg ctttgggatt taaggaagca a aactagagg    3600 atcgacagta tggtttagtg gacaatgaag ctgctgttgc acttgcaaat g gggcttcca    3660 acctctatgc attccgcctg catcacgggc acaaccacca ccaccatctc c ctaatcttc    3720 accttggaga tggatttgga gcccatgaac ttcgccttcc ttgagtggtg c ttgaggtcg    3780 accttccagc tcttcagaca tcttatctaa atgcgtgtgc taactagaga t gctatctaa    3840 tattatttaa taattaatta agagcccgga agtaaaaaat actttcatag a ttgtaattt    3900 acctcagggt aatgtgtatg gcagcatatt agattgtgat ttgagcaagg a atgtcattc    3960 cttatggatt aattaaatat aaaagctctt tttcacaaat ataattccac t ggagtagc     4020 attctgcaat atcccatatg atctgcaggc ttaataatta tatgattgaa a tgtgttgga    4080 tcaaccgtca tatgtatgta tgtatgtatg tatgtatacg tatgtgtata c tagggagtc    4140 aacaacacag ggggtgtaag caccaaatgc attatccact gttttttgccc a aaccccatt    4200 tggcataggt cgacaatacc ataccaatgc ctccgaagcc atccttcccc g ccgccctac    4260 acaaaccaaa accgctgaat tcctg                                           4285
```

<210> SEQ ID NO 2
<211> LENGTH: 946
<212> TYPE: DNA
<213> ORGANISM: Populus balsamifera subsp. trichoc arpa
<220> FEATURE:
<221> NAME/KEY: CDS
<222> LOCATION: (1)..(684)

<400> SEQUENCE: 2

```
atg ggt cgt gga aag att gaa atc aag aag a tc gaa aac ccc aca aac       48
Met Gly Arg Gly Lys Ile Glu Ile Lys Lys I le Glu Asn Pro Thr Asn
 1               5                  10                  15 agg caa gtc acc tac tcg aag aga aga aat g gt att ttc aag aaa gcc       96
Arg Gln Val Thr Tyr Ser Lys Arg Arg Asn G ly Ile Phe Lys Lys Ala
             20                  25                  30 caa gaa ctc act gta ctt tgt gat gct aag g tc tct ctt atc atg ttc      144
Gln Glu Leu Thr Val Leu Cys Asp Ala Lys V al Ser Leu Ile Met Phe
         35                  40                  45 tcc aac act aac aaa ctc aat gag tac att a gc ccc tcc aca tcg aca      192
Ser Asn Thr Asn Lys Leu Asn Glu Tyr Ile S er Pro Ser Thr Ser Thr
     50                  55                  60 aag aag atc tac gat caa tat cag aac gct t ta ggc ata gat ctg tgg      240
Lys Lys Ile Tyr Asp Gln Tyr Gln Asn Ala L eu Gly Ile Asp Leu Trp
 65                  70                  75                  80
```

-continued

```
ggc act caa tac gag aaa atg caa gag cac t tg agg aag ctg aat gat      288
Gly Thr Gln Tyr Glu Lys Met Gln Glu His L eu Arg Lys Leu Asn Asp
             85                  90                  95 atc aat cat aag ctg aga caa gaa atc agg c ag agg aga gga gag ggc      336
Ile Asn His Lys Leu Arg Gln Glu Ile Arg G ln Arg Arg Gly Glu Gly
        100                 105                 110 ctg aat gat ctg agc att gat cat ctg cgc g gt ctt gag caa cat atg      384
Leu Asn Asp Leu Ser Ile Asp His Leu Arg G ly Leu Glu Gln His Met
            115                 120                 125 act gaa gcc ttg aat ggt gtg cgt ggc agg a ag tac cat gtg atc aaa      432
Thr Glu Ala Leu Asn Gly Val Arg Gly Arg L ys Tyr His Val Ile Lys
        130                 135                 140 aca caa aac gaa acc tac agg aag aag gtg a ag aat tta gag gag aga      480
Thr Gln Asn Glu Thr Tyr Arg Lys Lys Val L ys Asn Leu Glu Glu Arg
145                 150                 155                 160 cat gga aac ctc ttg atg gaa tat gaa gca a aa cta gag gat cga cag      528
His Gly Asn Leu Leu Met Glu Tyr Glu Ala L ys Leu Glu Asp Arg Gln
                165                 170                 175 tat ggt tta gtg gac aat gaa gct gct gtt g ca ctt gca aat ggg gct      576
Tyr Gly Leu Val Asp Asn Glu Ala Ala Val A la Leu Ala Asn Gly Ala
            180                 185                 190 tcc aac ctc tat gca ttc cgc ctg cat cac g gg cac aac cac cac cac      624
Ser Asn Leu Tyr Ala Phe Arg Leu His His G ly His Asn His His His
        195                 200                 205 cat ctc cct aat ctt cac ctt gga gat gga t tt gga gcc cat gaa ctt      672
His Leu Pro Asn Leu His Leu Gly Asp Gly P he Gly Ala His Glu Leu
    210                 215                 220 cgc ctt cct tga gtggtgcttg aggtcgacct tccagctctt c agacatctt         724
Arg Leu Pro
225 atctaaatgc gtgtgctaac tagagatgct atctaatatt atttaataat t aattaagag   784 cccggaagta aaaatactt ccatagattg taatttacct cagggtaatg t gtatggcag    844 catattagat tgtgatttga gcaaggaatg tcattcctta tggattaatt a aatataaaa   904 gctctttttc acaaataaaa aaaaaaaaaa aaaaaaaaaa aa                        946

<210> SEQ ID NO 3
<211> LENGTH: 681
<212> TYPE: DNA
<213> ORGANISM: Populus balsamifera subsp. trichoc arpa
<220> FEATURE:
<221> NAME/KEY: CDS
<222> LOCATION: (1)..(681)

<400> SEQUENCE: 3 atg ggt cgt gga aag att gaa atc aag aag a tc gaa aac ccc aca aac      48
Met Gly Arg Gly Lys Ile Glu Ile Lys Lys I le Glu Asn Pro Thr Asn
  1               5                  10                  15 agg caa gtc acc tac tcg aag aga aga aat g gt att ttc aag aaa gcc      96
Arg Gln Val Thr Tyr Ser Lys Arg Arg Asn G ly Ile Phe Lys Lys Ala
             20                  25                  30 caa gaa ctc act gta ctt tgt gat gct aag g tc tct ctt atc atg ttc     144
Gln Glu Leu Thr Val Leu Cys Asp Ala Lys V al Ser Leu Ile Met Phe
         35                  40                  45 tcc aac act aac aaa ctc aat gag tac att a gc ccc tcc aca tcg aca     192
Ser Asn Thr Asn Lys Leu Asn Glu Tyr Ile S er Pro Ser Thr Ser Thr
     50                  55                  60 aag aag atc tac gat caa tat cag aac gct t ta ggc ata gat ctg tgg     240
Lys Lys Ile Tyr Asp Gln Tyr Gln Asn Ala L eu Gly Ile Asp Leu Trp
 65                  70                  75                  80
```

```
ggc act caa tac gag aaa atg caa gag cac t tg agg aag ctg aat gat    288
Gly Thr Gln Tyr Glu Lys Met Gln Glu His L eu Arg Lys Leu Asn Asp
             85                  90                  95 atc aat cat aag ctg aga caa gaa atc agg c ag agg aga gga gag ggc    336
Ile Asn His Lys Leu Arg Gln Glu Ile Arg G ln Arg Arg Gly Glu Gly
        100                 105                 110 ctg aat gat ctg agc att gat cat ctg cgc g gt ctt gag caa cat atg    384
Leu Asn Asp Leu Ser Ile Asp His Leu Arg G ly Leu Glu Gln His Met
            115                 120                 125 act gaa gcc ttg aat ggt gtg cgt ggc agg a ag tac cat gtg atc aaa    432
Thr Glu Ala Leu Asn Gly Val Arg Gly Arg L ys Tyr His Val Ile Lys
    130                 135                 140 aca caa aac gaa acc tac agg aag aag gtg a ag aat tta gag gag aga    480
Thr Gln Asn Glu Thr Tyr Arg Lys Lys Val L ys Asn Leu Glu Glu Arg
145                 150                 155                 160 cat gga aac ctc ttg atg gaa tat gaa gca a aa cta gag gat cga cag    528
His Gly Asn Leu Leu Met Glu Tyr Glu Ala L ys Leu Glu Asp Arg Gln
                165                 170                 175 tat ggt tta gtg gac aat gaa gct gct gtt g ca ctt gca aat ggg gct    576
Tyr Gly Leu Val Asp Asn Glu Ala Ala Val A la Leu Ala Asn Gly Ala
            180                 185                 190 tcc aac ctc tat gca ttc cgc ctg cat cac g gg cac aac cac cac cac    624
Ser Asn Leu Tyr Ala Phe Arg Leu His His G ly His Asn His His His
        195                 200                 205 cat ctc cct aat ctt cac ctt gga gat gga t tt gga gcc cat gaa ctt    672
His Leu Pro Asn Leu His Leu Gly Asp Gly P he Gly Ala His Glu Leu
    210                 215                 220 cgc ctt cct                                                         681
Arg Leu Pro
225

<210> SEQ ID NO 4
<211> LENGTH: 227
<212> TYPE: PRT
<213> ORGANISM: Populus balsamifera subsp. trichoc arpa

<400> SEQUENCE: 4

Met Gly Arg Gly Lys Ile Glu Ile Lys Lys I le Glu Asn Pro Thr Asn
 1               5                  10                  15

Arg Gln Val Thr Tyr Ser Lys Arg Arg Asn G ly Ile Phe Lys Lys Ala
            20                  25                  30

Gln Glu Leu Thr Val Leu Cys Asp Ala Lys V al Ser Leu Ile Met Phe
        35                  40                  45

Ser Asn Thr Asn Lys Leu Asn Glu Tyr Ile S er Pro Ser Thr Ser Thr
    50                  55                  60

Lys Lys Ile Tyr Asp Gln Tyr Gln Asn Ala L eu Gly Ile Asp Leu Trp
65                  70                  75                  80

Gly Thr Gln Tyr Glu Lys Met Gln Glu His L eu Arg Lys Leu Asn Asp
                85                  90                  95

Ile Asn His Lys Leu Arg Gln Glu Ile Arg G ln Arg Arg Gly Glu Gly
            100                 105                 110

Leu Asn Asp Leu Ser Ile Asp His Leu Arg G ly Leu Glu Gln His Met
        115                 120                 125

Thr Glu Ala Leu Asn Gly Val Arg Gly Arg L ys Tyr His Val Ile Lys
    130                 135                 140

Thr Gln Asn Glu Thr Tyr Arg Lys Lys Val L ys Asn Leu Glu Glu Arg
145                 150                 155                 160

His Gly Asn Leu Leu Met Glu Tyr Glu Ala L ys Leu Glu Asp Arg Gln
```

-continued

```
                165                 170                 175
Tyr Gly Leu Val Asp Asn Glu Ala Ala Val A la Leu Ala Asn Gly Ala
                    180                 185                 190

Ser Asn Leu Tyr Ala Phe Arg Leu His His G ly His Asn His His His
        195                 200                 205

His Leu Pro Asn Leu His Leu Gly Asp Gly P he Gly Ala His Glu Leu
    210                 215                 220

Arg Leu Pro
225

<210> SEQ ID NO 5
<211> LENGTH: 5656
<212> TYPE: DNA
<213> ORGANISM: Populus balsamifera subsp. trichoc arpa

<400> SEQUENCE: 5
agtatatata ctaaataaat atataaactt gtaaaaaata aaagaaaaat a atcattgca      60 tgcaaactaa acaaacatta aaattatact taaacaaaac taatctaaaa t gaagttttt    120 aaaaggtaat tatgacatag ccacgagcca ctcaataaac ctttataaga t ttaaattga   180 tgctaaaata tattttttt tattttttgc atcattaaag aaataactca a aagcatctt    240 ttattttta aatattaatt tattagaaca atacttgata tctattgaaa t aatactcaa    300 tatctatcta taaatcaaaa aacctaaact ctagattgta aaaaataata a taatagaag   360 agccacccat ccaaaacttc tatattattt gacttgaaag caaaaacatt a atacacata   420 attcatgaaa atactcatg aaagtctata attcacaaaa gaattgatga a tattcatat    480 atagttcact aataacattc attttcatca tataattaac gtattaattc a agtactaaa   540 atatttatg aactaaaaga aattattgat caaagaaaga ctcaataaca a atattttt    600 tattaatcaa actcaaattc aaattcatga accctcaaat ccattatcaa a tccataaac   660 ctatttgggg tttgagattt ttgttatcca agggttttat ggagacaatt t atcattccc   720 ttttattag tcttttttat tatatattaa tattttatat taaaatacta a ttacaaaat   780 tcaatatgat tttaatcttg gacctcatat ataattccgc tttaaaactc c gactcatat   840 tctaaaccca attccaacat ggactaaaca attaatccca atattagagg g aacaaatta   900 tttatttctt aacaacacga aaactaaagt atatcactct gcaaaatgta a ttacaagtc   960 cttcgtgttt aggctagttt gaagatgcct gtggttggag accagagaca t caaattaat  1020 gttttttat agtaacatgt gctcaagttg catgcatttt tcgtaccaac a aaatacatg  1080 taaaatcatc atccattaat caaattgcaa tgattcatag catatgcata a cgcatgtgt  1140 ctgtgcatgt tttagctggt tcaattcttg cagattgtac tgctaaatgt a cgtactagc  1200 acctcaaatc acagtgacct cccaaatatt gcacagacct ctttgtttac a aatttcaag  1260 catcctaatt aatctcccaa gtgacatctg gtggccatgt tgcggccctg a caagcagct  1320 gagaaattct ccaacattag agggattcaa tgttctgttc aatgtttgga t acattgatt  1380 ctgcattgca acgctaatca cggtctgttc tccggcaagg gggggaaaaa c aatgatcag  1440 ggataaggca gcgaatgtct ggtgaaaaca agggtatttt catacttttc t caggttcgt  1500 gtagtcagca atgaacgaaa cgaggcaaat ccaaccaagt agaaaaacct c atgagtaac  1560 gagaaagtcg aggagacagt atctggcacc ctcagatgca tcataccttg c gatgagcca  1620 gaaactaaga tgattctagt gacgtctaaa tcatcaatcc cacggttaaa a ggacaccat  1680 aacccaagcc actagaatat ctgcttacgc agcaaccaca ctgcaaagcc a cgacgaaga  1740
```

-continued

```
actacaaaga tacggatata acatgatata aatatattaa tacttaattc t tcaaggtct    1800
tggattatga actttttttgt tcatatttat tttattatat tgaaaaactc g aaataaata   1860
agacgattat tataagaatt cttaaatcat gtttatcaaa ttttgtccta t ctagagacc    1920
attaataatt gtgtgtggat taattcacca aaaacttaaa tgaaaagtaa c tttatctat    1980
ctagagatgg aaaaggaact caattaccct caataataaa attggatgga a atcatctag   2040
atggtggtcc agtagtaaga ttttgggact aaaaggtttg ttctctttgt g gtctcaggt   2100
tcgagccatg tggttgctta tatgatgacc actgaaaatt tacatggtcg t taacttcag   2160
ggcccgtggg attagtcgag gtgcgtcaag ttagtctgga cacccatatt a atctaaaaa   2220
aaaaaattaa atggcaaaaa atattttgaa tgttgaagta aaaaaagtga a agggaggta   2280
gtaaaacaat atacgaccta acaggagagg agtccaatca agtagatcat g tgtcaagag   2340
atgagtggat agaagaactt caagtgaaga atgtatgcag ggaaccaaat g tgtgaatga   2400
cacaaagatc tgactagttc gatttcaact gtccagttcc gaagaaacat c aaaccctt    2460
taattctgtt agcttcccaa tacatacaaa aaagaaaaaa agcaaaaaa c tcgtcctgt    2520
taagggcagt tttggtatat aaataaaaca agaagctcac ttgtctttat a tatctacca   2580
aatccaagac atgcacctgt gaaagatcac agagagagag acaaggggc a gatagatat    2640
ggatccggag gctttcacgg cgagtttgtt caaatgggat acgagagcaa t ggtgccaca   2700
tcctaaccgt ctgcttgaaa tggtgccccc gcctcagcag ccaccggctg c ggcgtttgc   2760
tgtaaggcca agggagctat gtgggctaga ggagttgttt caagcttatg g tattaggta   2820
ctacacggca gcaaaaatag ctgaactcgg gttcacagtg aacacccttt t ggacatgaa   2880
agacgaggag cttgatgaaa tgatgaatag tttgtctcag atctttaggt g ggatcttct   2940
tgttggtgag aggtatggta ttaaagctgc tgttagagct gaaagaagaa g gcttgatga   3000
ggaggatcct aggcgtaggc aattgctctc tggtgataat aatacaaata c tcttgatgc   3060
tctctcccaa gaaggtttgg ttagcattga ttctacctttt tagtgtaatt a agctaagct   3120
catactatta ctagctatag gagtccatgg ccaatttgtt gtagttttgt a gagtaaatt   3180
aattctatgt atacttggat aagataatta gcttattata agatgttact t gccagctta   3240
taatttccat atacaacaat cattttcatt ccctttttcct tttcttatat a tgaaattta   3300
gttcaagtat aagtgcttgt acaccaatgt atgtttactc tagtcatatc a attctactt   3360
tgcagggttg gtttcttgct aattaatcac catgctcaat attagagtag t aattctctt   3420
aactaagtcc aggttagcta gcttttggtt tcttgttaat tgccgcacat a cttagctta   3480
aattagttct caaggtaata gttagcttaa tagctttgag ctcatactgg t ttctataaa   3540
ataaatgaac aaaatctgat tgtttcgaaa aattaaataa cattaactta t taaacttat   3600
tttcctttcc ttaattttta attttttgctt gtttcttggg tggttgtgtg t tcaggtttc   3660
tctgaggagc cagtacagca agacaaggag gcagcaggga gcggtggaag a gggacatgg   3720
gaggcagtgg cagcggggga gaggaagaaa cagtcagggc ggaagaaagg c caaagaaag   3780
gtggtggacc ttgatggaga tgatgaacat ggtggtgcta tctgtgagag a cagcgggag   3840
cacccattca ttgtaacaga gcctggtgaa gtggcacgtg gcaaaaagaa c ggtcttgat   3900
tacctcttcc atttatatga acagtgtcgt gatttcttga tccaagtcca a agcattgcg   3960
aaggagaggg gagaaaaatg cccccactaag gtacgaagag tcagcttcgc g agggattga   4020
ttttttattta gaaatatatt aaaataatat tttttatatt ttaaaattta t ttttaatat   4080
```

-continued

```
taatatatta aaataatata aaaatactga aaaataattt tttaaaaaat a attttttt      4140 caaaaatatt tacaaaacaa actgtgtcta agaacacat ttagaccgtt a atttctgca       4200 agtctcaaca tttcaatggt tcttgtcttg gacccacata gaccagccat t gtattctgg      4260 actggactgg agtatgccc ccacctgaat tgcctttca cagctgtccc g ataaaaacg        4320 tgacaactca tgtactggtt tctggtccct gtcattttag acctgctatt t gcagtggga      4380 tacttattgg ttactcttac tagtcgatca tcgttatttg aatatttcaa a tattctgat     4440 tttggaagtt tgtacgatgt cgtgtcacgt ggatcttgtg aaacctggtt g atgtcaact     4500 attgtcgaac tggaccaaaa tccattacat tctgagtttc tctagtgttt t cctgccatg    4560 gaacctgaaa gccatgttg atggttagga cttagaattt gattagccct a aatggaaca    4620 gtgagtaatt atgctaagaa aaatggtttt ttttgtttt gttttgtgtt t ggttatagg     4680 tgacaaatca ggtgtttagg tatgccaaga aggcaggagc aagctacatc a acaagccca  4740 aaatgagaca ctacgtgcat tgctatgctt tacattgcct cgatgaggac g catccaatg    4800 cacttaggag agcgttcaag gagagaggag aaaatgttgg agcatggaga c aggcttgtt    4860 acaagcccct tgtagccatc gcatcacgcc aaggctggga catagattcc a ttttcaatg   4920 ctcatcctcg gcttgccatt tggtatgtgc cgaccaagct ccgtcaactt t gttatgcag   4980 agcgcaatag tgccacttct tcaagctctg tctctggtac tggaggtcac c tgccgtttt    5040 gagttcttaa ttatgccaag ataaatactc ctatctctat aaaattgtca a aatgtatgt   5100 tgtagcgagg tcaggacaaa gtattggttg atggaggatg gttcattaaa t ttcacatcc    5160 ttgactattt atatatcatg atatgcttaa aggctctaat cattgtttac g tcgatggaa   5220 ctattatatt tctaatttag ttttcaggga agtctaggct gctggtgcct a cagtgtcca   5280 taaatttgag caaaatggcc aaaagggcc aattgggacc cactaaatta a tttggtggt    5340 gcagtccccc ttacaatacg actgcatgta atacttgtcc aaaatttgag t gcagttcat    5400 aggctgttac tttaaacaga caaacacatg atgacaagat aaaaggcatg g ataattctt    5460 gtcttcttga ggtgccaaca tgcaaaatgc catgtcaggt tgttgatttg a tttctaatt    5520 gttaaccatt actgttttt ttgccataac catgcaatgg tgctaaagtt a gatgccata    5580 aaagatgtat catggcagcc tgcaatgcaa ataaaaacgg ggaacaatg g aaagttgcc    5640 agaaatttca attact                                                     5656
```

<210> SEQ ID NO 6
<211> LENGTH: 1308
<212> TYPE: DNA
<213> ORGANISM: Populus balsamifera subsp. trichoc arpa
<220> FEATURE:
<221> NAME/KEY: CDS
<222> LOCATION: (12)..(1145)

<400> SEQUENCE: 6

```
ggcagataga t atg gat ccg gag gct ttc acg gcg  agt ttg ttc aaa tgg       50
            Met Asp Pro Glu Ala Phe Thr Ala Ser Leu Phe Lys Trp
              1               5                  10 gat acg aga gca atg gtg cca cat cct aac c gt ctg ctt gaa atg gtg        98
Asp Thr Arg Ala Met Val Pro His Pro Asn A rg Leu Leu Glu Met Val
     15                  20                  25 ccc ccg cct cag cag cca ccg gct gcg gcg t tt gct gta agg cca agg      146
Pro Pro Pro Gln Gln Pro Pro Ala Ala Ala P he Ala Val Arg Pro Arg
 30                  35                  40                  45 gag cta tgt ggg cta gag gag ttg ttt caa g ct tat ggt att agg tac      194
Glu Leu Cys Gly Leu Glu Glu Leu Phe Gln A la Tyr Gly Ile Arg Tyr
```

-continued

```
                    50                    55                       60
tac acg gca gca aaa ata gct gaa ctc ggg t tc aca gtg aac acc ctt        242
Tyr Thr Ala Ala Lys Ile Ala Glu Leu Gly P he Thr Val Asn Thr Leu
                    65                  70                  75 ttg gac atg aaa gac gag gag ctt gat gaa a tg atg aat agt ttg tct        290
Leu Asp Met Lys Asp Glu Glu Leu Asp Glu M et Met Asn Ser Leu Ser
            80                  85                  90 cag atc ttt agg tgg gat ctt ctt gtt ggt g ag agg tat ggt att aaa        338
Gln Ile Phe Arg Trp Asp Leu Leu Val Gly G lu Arg Tyr Gly Ile Lys
        95                  100                 105 gct gct gtt aga gct gaa aga aga agg ctt g at gag gag gat cct agg        386
Ala Ala Val Arg Ala Glu Arg Arg Arg Leu A sp Glu Glu Asp Pro Arg
110             115                 120                 125 cgt agg caa ttg ctc tct ggt gat aat aat a ca aat act ctt gat gct        434
Arg Arg Gln Leu Leu Ser Gly Asp Asn Asn T hr Asn Thr Leu Asp Ala
                130                 135                 140 ctc tcc caa gaa ggt ttc tct gag gag cca g ta cag caa gac aag gag        482
Leu Ser Gln Glu Gly Phe Ser Glu Glu Pro V al Gln Gln Asp Lys Glu
            145                 150                 155 gca gca ggg agc ggt gga aga ggg aca tgg g aa gca gtg gca gcg ggg        530
Ala Ala Gly Ser Gly Gly Arg Gly Thr Trp G lu Ala Val Ala Ala Gly
        160                 165                 170 gag agg aag aaa cag tca ggg cgg aag aaa g gc caa aga aag gtg gtg        578
Glu Arg Lys Lys Gln Ser Gly Arg Lys Lys G ly Gln Arg Lys Val Val
175             180                 185 gac ctt gat gga gat gat gaa cat ggt ggt g ct atc tgt gag aga cag        626
Asp Leu Asp Gly Asp Asp Glu His Gly Gly A la Ile Cys Glu Arg Gln
190             195                 200                 205 cgg gag cac cca ttc att gta aca gag cct g gt gaa gtg gca cgt ggc        674
Arg Glu His Pro Phe Ile Val Thr Glu Pro G ly Glu Val Ala Arg Gly
                210                 215                 220 aaa aag aac ggt ctt gat tac ctc ttc cat t ta tat gaa cag tgt cgt        722
Lys Lys Asn Gly Leu Asp Tyr Leu Phe His L eu Tyr Glu Gln Cys Arg
            225                 230                 235 gat ttc ttg atc caa gtc caa agc att gcg a ag gag agg gga gaa aaa        770
Asp Phe Leu Ile Gln Val Gln Ser Ile Ala L ys Glu Arg Gly Glu Lys
        240                 245                 250 tgc ccc act aag gtg aca aat cag gtg ttt a gg tat gcc aag aag gca        818
Cys Pro Thr Lys Val Thr Asn Gln Val Phe A rg Tyr Ala Lys Lys Ala
255             260                 265 gga gca agc tac atc aac aag ccc aaa atg a ga cac tac gtg cat tgc        866
Gly Ala Ser Tyr Ile Asn Lys Pro Lys Met A rg His Tyr Val His Cys
270             275                 280                 285 tat gct tta cat tgc ctc gat gag gac gca t cc aat gca ctt agg aga        914
Tyr Ala Leu His Cys Leu Asp Glu Asp Ala S er Asn Ala Leu Arg Arg
                290                 295                 300 gcg ttc aag gag aga gga gaa aat gtt gga g ca tgg aga cag gct tgt        962
Ala Phe Lys Glu Arg Gly Glu Asn Val Gly A la Trp Arg Gln Ala Cys
            305                 310                 315 tac aag ccc ctt gta gcc atc gca tca cgc c aa ggc tgg gac ata gat       1010
Tyr Lys Pro Leu Val Ala Ile Ala Ser Arg G ln Gly Trp Asp Ile Asp
        320                 325                 330 tcc att ttc aat gct cat cct cgg ctt gcc a tt tgg tat gtg ccg acc       1058
Ser Ile Phe Asn Ala His Pro Arg Leu Ala I le Trp Tyr Val Pro Thr
335             340                 345 aag ctc cgt caa ctt tgt tat gca gag cgc a at agt gcc act tct tca       1106
Lys Leu Arg Gln Leu Cys Tyr Ala Glu Arg A sn Ser Ala Thr Ser Ser
350             355                 360                 365 agc tct gtc tct ggt act gga ggt cac ctg c cg ttt tga gttcttaatt       1155
```

Ser Ser Val Ser Gly Thr Gly Gly His Leu Pro Phe
                370                 375 atgccaagat aaatactcct atctctataa aattgtcaaa atgtatgttg t agcgaggtc     1215 aggacaaagt attggttgat ggaggatggt tcattaaatt tcacatcctt g actatttat     1275 atatcatgat atgcttaaag gctctaaaaa aaa     1308

<210> SEQ ID NO 7
<211> LENGTH: 1131
<212> TYPE: DNA
<213> ORGANISM: Populus balsamifera subsp. trichoc arpa
<220> FEATURE:
<221> NAME/KEY: CDS
<222> LOCATION: (1)..(1131)

<400> SEQUENCE: 7 atg gat ccg gag gct ttc acg gcg agt ttg t tc aaa tgg gat acg aga     48
Met Asp Pro Glu Ala Phe Thr Ala Ser Leu P he Lys Trp Asp Thr Arg
 1               5                  10                  15 gca atg gtg cca cat cct aac cgt ctg ctt g aa atg gtg ccc ccg cct     96
Ala Met Val Pro His Pro Asn Arg Leu Leu G lu Met Val Pro Pro Pro
             20                  25                  30 cag cag cca ccg gct gcg gcg ttt gct gta a gg cca agg gag cta tgt     144
Gln Gln Pro Pro Ala Ala Ala Phe Ala Val A rg Pro Arg Glu Leu Cys
         35                  40                  45 ggg cta gag gag ttg ttt caa gct tat ggt a tt agg tac tac acg gca     192
Gly Leu Glu Glu Leu Phe Gln Ala Tyr Gly I le Arg Tyr Tyr Thr Ala
     50                  55                  60 gca aaa ata gct gaa ctc ggg ttc aca gtg a ac acc ctt ttg gac atg     240
Ala Lys Ile Ala Glu Leu Gly Phe Thr Val A sn Thr Leu Leu Asp Met
 65                  70                  75                  80 aaa gac gag gag ctt gat gaa atg atg aat a gt ttg tct cag atc ttt     288
Lys Asp Glu Glu Leu Asp Glu Met Met Asn S er Leu Ser Gln Ile Phe
                 85                  90                  95 agg tgg gat ctt ctt gtt ggt gag agg tat g gt att aaa gct gct gtt     336
Arg Trp Asp Leu Leu Val Gly Glu Arg Tyr G ly Ile Lys Ala Ala Val
            100                 105                 110 aga gct gaa aga aga agg ctt gat gag gag g at cct agg cgt agg caa     384
Arg Ala Glu Arg Arg Arg Leu Asp Glu Glu A sp Pro Arg Arg Arg Gln
        115                 120                 125 ttg ctc tct ggt gat aat aat aca aat act c tt gat gct ctc tcc caa     432
Leu Leu Ser Gly Asp Asn Asn Thr Asn Thr L eu Asp Ala Leu Ser Gln
    130                 135                 140 gaa ggt ttc tct gag gag cca gta cag caa g ac aag gag gca gca ggg     480
Glu Gly Phe Ser Glu Glu Pro Val Gln Gln A sp Lys Glu Ala Ala Gly
145                 150                 155                 160 agc ggt gga aga ggg aca tgg gaa gca gtg g ca gcg ggg gag agg aag     528
Ser Gly Gly Arg Gly Thr Trp Glu Ala Val A la Ala Gly Glu Arg Lys
                165                 170                 175 aaa cag tca ggg cgg aag aaa ggc caa aga a ag gtg gtg gac ctt gat     576
Lys Gln Ser Gly Arg Lys Lys Gly Gln Arg L ys Val Val Asp Leu Asp
            180                 185                 190 gga gat gat gaa cat ggt ggt gct atc tgt g ag aga cag cgg gag cac     624
Gly Asp Asp Glu His Gly Gly Ala Ile Cys G lu Arg Gln Arg Glu His
        195                 200                 205 cca ttc att gta aca gag cct ggt gaa gtg g ca cgt ggc aaa aag aac     672
Pro Phe Ile Val Thr Glu Pro Gly Glu Val A la Arg Gly Lys Lys Asn
    210                 215                 220 ggt ctt gat tac ctc ttc cat tta tat gaa c ag tgt cgt gat ttc ttg     720
Gly Leu Asp Tyr Leu Phe His Leu Tyr Glu G ln Cys Arg Asp Phe Leu
225                 230                 235                 240

-continued

```
atc caa gtc caa agc att gcg aag gag agg g ga gaa aaa tgc ccc act      768
Ile Gln Val Gln Ser Ile Ala Lys Glu Arg G ly Glu Lys Cys Pro Thr
            245                 250                 255 aag gtg aca aat cag gtg ttt agg tat gcc a ag aag gca gga gca agc      816
Lys Val Thr Asn Gln Val Phe Arg Tyr Ala L ys Lys Ala Gly Ala Ser
            260                 265                 270 tac atc aac aag ccc aaa atg aga cac tac g tg cat tgc tat gct tta      864
Tyr Ile Asn Lys Pro Lys Met Arg His Tyr V al His Cys Tyr Ala Leu
            275                 280                 285 cat tgc ctc gat gag gac gca tcc aat gca c tt agg aga gcg ttc aag      912
His Cys Leu Asp Glu Asp Ala Ser Asn Ala L eu Arg Arg Ala Phe Lys
        290                 295                 300 gag aga gga gaa aat gtt gga gca tgg aga c ag gct tgt tac aag ccc      960
Glu Arg Gly Glu Asn Val Gly Ala Trp Arg G ln Ala Cys Tyr Lys Pro
305                 310                 315                 320 ctt gta gcc atc gca tca cgc caa ggc tgg g ac ata gat tcc att ttc     1008
Leu Val Ala Ile Ala Ser Arg Gln Gly Trp A sp Ile Asp Ser Ile Phe
            325                 330                 335 aat gct cat cct cgg ctt gcc att tgg tat g tg ccg acc aag ctc cgt     1056
Asn Ala His Pro Arg Leu Ala Ile Trp Tyr V al Pro Thr Lys Leu Arg
            340                 345                 350 caa ctt tgt tat gca gag cgc aat agt gcc a ct tct tca agc tct gtc     1104
Gln Leu Cys Tyr Ala Glu Arg Asn Ser Ala T hr Ser Ser Ser Ser Val
            355                 360                 365 tct ggt act gga ggt cac ctg ccg ttt                                  1131
Ser Gly Thr Gly Gly His Leu Pro Phe
        370                 375

<210> SEQ ID NO 8
<211> LENGTH: 377
<212> TYPE: PRT
<213> ORGANISM: Populus balsamifera subsp. trichoc arpa

<400> SEQUENCE: 8

Met Asp Pro Glu Ala Phe Thr Ala Ser Leu P he Lys Trp Asp Thr Arg
 1               5                  10                  15

Ala Met Val Pro His Pro Asn Arg Leu Leu G lu Met Val Pro Pro Pro
            20                  25                  30

Gln Gln Pro Pro Ala Ala Ala Phe Ala Val A rg Pro Arg Glu Leu Cys
        35                  40                  45

Gly Leu Glu Glu Leu Phe Gln Ala Tyr Gly I le Arg Tyr Tyr Thr Ala
    50                  55                  60

Ala Lys Ile Ala Glu Leu Gly Phe Thr Val A sn Thr Leu Leu Asp Met
65                  70                  75                  80

Lys Asp Glu Glu Leu Asp Glu Met Met Asn S er Leu Ser Gln Ile Phe
                85                  90                  95

Arg Trp Asp Leu Leu Val Gly Arg Tyr G ly Ile Lys Ala Ala Val
            100                 105                 110

Arg Ala Glu Arg Arg Leu Asp Glu Glu A sp Pro Arg Arg Arg Gln
        115                 120                 125

Leu Leu Ser Gly Asp Asn Asn Thr Asn Thr L eu Asp Ala Leu Ser Gln
    130                 135                 140

Glu Gly Phe Ser Glu Glu Pro Val Gln Gln A sp Lys Glu Ala Ala Gly
145                 150                 155                 160

Ser Gly Gly Arg Gly Thr Trp Glu Ala Val A la Ala Gly Glu Arg Lys
                165                 170                 175

Lys Gln Ser Gly Arg Lys Lys Gly Gln Arg L ys Val Val Asp Leu Asp
```

```
                       180                  185                  190
Gly Asp Asp Glu His Gly Gly Ala Ile Cys Glu Arg Gln Arg Glu His
        195                  200                  205

Pro Phe Ile Val Thr Glu Pro Gly Glu Val Ala Arg Gly Lys Lys Asn
    210                  215                  220

Gly Leu Asp Tyr Leu Phe His Leu Tyr Glu Gln Cys Arg Asp Phe Leu
225                  230                  235                  240

Ile Gln Val Gln Ser Ile Ala Lys Glu Arg Gly Glu Lys Cys Pro Thr
                245                  250                  255

Lys Val Thr Asn Gln Val Phe Arg Tyr Ala Lys Lys Ala Gly Ala Ser
            260                  265                  270

Tyr Ile Asn Lys Pro Lys Met Arg His Tyr Val His Cys Tyr Ala Leu
        275                  280                  285

His Cys Leu Asp Glu Asp Ala Ser Asn Ala Leu Arg Arg Ala Phe Lys
    290                  295                  300

Glu Arg Gly Glu Asn Val Gly Ala Trp Arg Gln Ala Cys Tyr Lys Pro
305                  310                  315                  320

Leu Val Ala Ile Ala Ser Arg Gln Gly Trp Asp Ile Asp Ser Ile Phe
                325                  330                  335

Asn Ala His Pro Arg Leu Ala Ile Trp Tyr Val Pro Thr Lys Leu Arg
            340                  345                  350

Gln Leu Cys Tyr Ala Glu Arg Asn Ser Ala Thr Ser Ser Ser Ser Val
        355                  360                  365

Ser Gly Thr Gly Gly His Leu Pro Phe
    370                  375

<210> SEQ ID NO 9
<211> LENGTH: 11485
<212> TYPE: DNA
<213> ORGANISM: Populus balsamifera subsp. trichocarpa

<400> SEQUENCE: 9
ggatccacct ccacgtcagt ccatccgcat tcgtaagtcc ataaaactac cagattttgc    60
ttattcttgt tattcttcat catttacttc ctttttagct tctattcatt gccttttttga  120
gccctcttcc tataaagagg caattcttga tccgcttcgg caacaagcta tgaatgaaga  180
attttctgct ttgcataaga cagatacttg ggatctggtt cctctacctc ccggtaagag  240
tgttgttggt tgtcattggg tgtataagat caagactaat tctgatgggt ctattgagca  300
atacaaagct aggctggttg caaaaggata ctctcaacat tatggtatgg actatgagga  360
aacatttgcc ccggttgcaa aaatgactac tattcgtact cttattgtcg tagcttcgat  420
tcgtcagtgg catatttctc agcttgatgt taaaaatgcc ttcttgaatg gagatcttca  480
agaagaagtt tatgtggcac tccctcctgg tatttcatat gactctggat atgtttgtaa  540
gcttaagaaa gcattaatta tatggtctca acaagcacc ccgtgcttgg tttgagaaat  600
tctctattgt gatctcgtct cttggcattg tttctagcag tcatgattct gctcttttta  660
ttaagtgcac tgatgcaggt cgtatcattc tgtctttata tgttgataac atgattatta  720
ttggtgatga cattgatggt atttcagtct gaagacaaa gttggctaga cgatttgaaa  780
tgaaagattt gggttatctt caatatttcc tgggtattga ggtagcatac tcacctagag  840
gttaccttct ttctcagtcg aaatatgttg cagatattct tgagcagact agacttactg  900
ataacaaaac tgtagatact cctattgagg tcaacgtgag gtactcttct tctgatggtt  960
tacctttgat agatcttact ttataccaca ctattgttag gagtttggta tatctcacca 1020
```

```
ttactcgtcc agatattgca tatgctgttc atgttgttag tcagtttgtt g cttctctta    1080 ctactgttca ctgggcagct gttattcgta ttttgcgata tcttcggggt a cagttttc     1140 agagtctttt actttcatcc acctcttcct tggagttgcg tgcatactct g atgctgatc    1200 atggtagtga tcccacagat cgcaagtctg ttaccgggtt ctgtatcttt t taggtgatt    1260 ctcttatttc ttggaagagc aagaaacaat ctattgtttc tcaatcatcc a tcgaagcag    1320 aatatcgtgc catgacatct actaccaaag agattgtttg gttatgttgg t tacttgctg    1380 atatgagagt ttcattttct catcctactc ctatgtattg tgacaaccag a gttctattc    1440 agattgctca caactcggtt tttcatgagc gaactaagca cattgagatc g attgtcatc    1500 ttactcatca tcatctcaag catggcacca ttgcttacc ttttgttcct t cttccttac     1560 agattgcaga tttctttatc aaggcgcatt ccatctctcg ttttttgtttt c aggttggca   1620 aactctcgat gcttgtagct gccgcattgt gagtttgagg ggagatgtta a ataatattt    1680 atgtagtctt atttattaag ggtagaatag tactttcagt ttaacctata t atactttat    1740 ttgtatttag gttaagacta agcattcata ataaatgtat cattaagaat t ctagcctcc    1800 ttttcgtgtt tcattttaat tatttttaac aatcttgtat taatatatgt g aattgattg    1860 aattaaatct tgtaatacaa tttaattgat tctaagttaa acaatctgct g gggaacatt    1920 catacaacta tctttctttt cgtttcaagt aggcaggaaa taaaacgttt t tagtttagg    1980 tgactaaaca atggaattta atgaaataag ggtagagatg aggtctgagg t tatcttgtt    2040 aagcaccttc ccatttgaac catgatttg tcgttaagca ctgagagtgt a acttagccc     2100 taaaacgtct cactcacccc attataattc attttcagaa agtcccttgc t tttctctct    2160 aatgacctaa atcatttcct tgaaagccaa aaataaaaaa taaaaacgaa t atagtggag    2220 agttattgag gtctgaatct gacgacagat tcccacctttt agcctcttct t tttaattcc    2280 tcttcaatgc tcaccactca tcaataccaa gataagaaaa agaaaaaaaa a tggaaaaat    2340 tattgaagaa gagaaattac aaagacagta gttagacttg gtagaagtat t gttatatat    2400 aaagattgga tgagaggttg ttttcactt tataaatacc cacctcttag c ccaaacttg     2460 cttccatttt cttcatctct ctactagtta gatttgtagg agaaatccca a aggaaaaga    2520 tcctcacttt ctctacacat taactgctat ctacagcccc tagctacttt g ttttatttc    2580 ctcccaaggt tagttactaa aacatggagt cataaatctc gttgtattct t cagtgcttc    2640 atcacttgtt ttgggctaat taatcaatct tttcacgttt caaaacccac c tcttctttt    2700 tctgttttga tcactcagaa accccaaaaa atacaacttt caaacatttc t gtctccctt    2760 tcccatttca atctccagat tgaagcacca gtgatttatt tttgttttgt t gattgatta    2820 ttttgaccat aaccaataaa ccataacaat cgcaattcag aagctccaga c gttcatcga    2880 ccccttttc ttatgtttat tttatattac ttccatcctg gactactcat t tggacaaaa     2940 aaagtattgc taaatatgct atgagttgtg catatattat tcttgaatta g tagtatttt    3000 tttcattta ttcatttttt tgtgttgtca ctcagtttgt gttttggatc a gctagctag    3060 gctgcagcta tggaatatca aaatgaatcc cttgagagct ccccctgag g aagctggga    3120 aggggaaagg tggagatcaa gcggatcgag aacaccacca atcgccaagt c actttctgc   3180 aaaaggcgca gtggtttgct caagaaagcc tacgaattat ctgttctttg c gatgctgag    3240 gttgcactca tcgtcttctc tagccgcggt cgcctttatg agtactctaa c gataggtaa    3300 ataaatctaa ttttagatat ttgcttctct ggatcttaaa ttctccatgt t acaagccct    3360
```

```
ctatcttcat gtggtcactt tttttttttt tttatcttcc tttctgcccc a aagagattt    3420 ttttatcctc tctattttgc ttatgttagt gttaatttt agctttaatt g gtttctttc     3480 attttcattt tctttcttc atgaatgatc attaaatggt tttcaatttc t aaggtggga     3540 aatttattat tattattatt attttgtgtt taatctctgg gtaaaggatt t aaagcaaaa    3600 gagacacaat cattccttat gctgcagttt agattgagtt tcttatctaa c tgagattca    3660 cttgtctttc tttctttctt tctcttctct tacccttag acgatgctga t gcacacgtt    3720 attttgagtt cttggtttgg taaaaacata gatctggtat aataaacaga c atagaagca    3780 ctatatgagt gtagtatggt agcagaaata agtataggtc tgtgagatca g cctctttat   3840 ctcctcccctt gttgttaatt tgttgtttc cgttttttctt tctcttccat t attcctctt   3900 gcactctcta tctctcgctt ttttttttgca catacttgtt tgtttgtgtc a tctacgagg   3960 ctaaagagat tgcctatagc caaagctgtc atcttctcat tagtccaaac c ctccatctc    4020 ttttcacttc ctagttaaat agcacgtcaa ttagacatca agaaagcaaa a gtaccatgt    4080 caaataaccg tgaaaagaa gaagaacaaa gaaaggtttt tttaatttgt c atgtcactc    4140 aaacatatat tattagggtt tcaaatccca aatccccaga tgggttttc a tcttatttt    4200 attttttccaa accaatccag ggttttttccc ctaatcacac gaaatttccc a aaatctcag   4260 tttgaaccca cgagggata gtgaaaacct ttctgttagt caatgcataa c cccagttag    4320 ggttcatagt tagggttcat attcaagtaa ccacatgaaa tcatcgaaat c gtacattaa    4380 cattcaagga aaactgttaa atcaagcaag tggacccttc cacaaccaat c aaaactcag    4440 ttagatttca cctagatttt taccccttttt ttaacctggg taagtatggt a cagtaatcg   4500 gttagggttt agtagccagt caaatagatc agattgttgt tcgggtttat g aacagaatc    4560 tttggtaacg tcacacacga ttttttcagtt cttgcctact gacaaaaggc t ttatgtcat   4620 gattccttaa actgaaccca agatttttaa cttccgatcc ccctggaaaa a atatgaaat    4680 tccaaaatt gtccatttct tctccttaga tctctctcta tctctctccc g gttaaattg    4740 tttccatggt gaaagcagag agatggatca atgagaatgg gttaaccaag g ccataatga    4800 tggcactgtt taagatcttg tatagatata tttatataag tttttttttt t tttaattta    4860 aagagagatt tagccccatt tgtatttta cggtgagaaa acacttttat a aaaaattga   4920 tattttttta aaaattattt tttatatttt ttagattatt tttatgtgtt a atattaaaa    4980 ataaattttt taaaatataa aaaatattat attaatatat tttaaataaa a aattaaccg    5040 ttgatgacaa tattgagaga aagagagtcg tgaagagaga atgaacgaca a ctgttaacc    5100 agtggaagag ttctgtcaat tttggttct tctatgtaat agaaagccta c aactctagc    5160 tggtattgta cggctctgct tctctcagag tttcagtctg agactaataa a atgtccgat    5220 tagtacaata ttttattaca atgaaataga atatcgaggt gggtaataga g tgagtttaa    5280 ggagattatc cactatgtaa tgggttattg acacgtggag aatatttgac c gctgatcta    5340 ccttggccaa tcatattgta ggattcagtg acagcttggc agagacagcc a atcaatgtc    5400 tcgacgaagt taaggtataa ggaaatctag aaaagcggtt cttgtctgaa t tgacaagat    5460 gtgttcacat tttactgaga ttattatggc aaaattttag gatttccttc g cattgtgtc    5520 gaggaaagac tggataatca gactgactcg gagagctgtg gttttgtcat t catcttctt    5580 tttagggttt tctacgagtt aacttaatgg agttattcgt tgatttgact g tttaattgc    5640 cttaccgtca agctttgtta taataaggat tttttaaatt gttttttttta t ttataaata    5700 tattaaaata atatttttta attttttaaga tggcatatca aaaatatttt a aaaaataaa    5760
```

-continued

```
aaaataattt gaaataaaac aaaaattaat tttttaaaa caatattttt a acgcaataa   5820
caaattctta atcttttact catatatctt aaatttacga gagttttttc c aaaaagata   5880
aagagatata tgtaagcgat aaagtattag taacctcaca taaaataatg t acaataata   5940
gataaaaact aaattttata taaaaattga atttcaatcc actttctttt t tcgtggatc   6000
ataaggagtt ggacttgctt ttttcacggt aatttgacca agaaagagt t aatacaaat   6060
aatattaatt aagatattat ctcttgttgt ttgttcttgt tttgaaataa t ttagttttt   6120
tttttaagaa aaaaagtttt ttccaataca taagcaaatac aaaagtgttt g aacatggta   6180
attcttcttc ttcttagttg accaaattac atttggtaga ctaaagttgt t catatatat   6240
gctaccattg atagagtcat tggccaatta tatgttttta cgtcattata t ttgaattct   6300
tttgttaata gtaattatta atcactgaag ttattgcatt cttgtcagct g ataaactcc   6360
aagttgtaat tttatgtttg atcttgtaat taagagcaag ccaggaggac a tctctagtg   6420
ttcgaggaaa ttgacaaaat ttgcttcctc aaatatattt ttgtttttca t tggacaaaa   6480
atacatgtta tatatatata tatatatata tatatatata tatatatata t aatgcctat   6540
attttgtgag tagttccata agtttaggat atgtttgagg tagtttaaca t aagcatttg   6600
attttttttt tcaatcctta tatcaaaatt atcataaaac aattaaaaaa t cattaattt   6660
atttttatttt tttaattaaa aaaaacactt ataaacacag tattacccaa a tacagattt   6720
atgaagccgc catgtggtaa aaaatacat gttagagata tcagaagttt a caagcatgt   6780
ttatatgcgt taatgtggca tatgaaatgt catatcaatt gcgttacaaa g cttttcttg   6840
tgctaagtgt ggcgttagta ataagcaagt gtttgtaaga attgtcaaca c gtgtgttta   6900
cttacttgaa agaacattaa ttgctaattt tattaaataa ttaatccttc c tattactat   6960
cttgggatag gttgaagagc ataaggaaaa gggttaccat gataaataca a aaaataaaa   7020
aaggaggaag gagtagtttt caatttatt ttaattgtca atactatgtg c ttggtgaaa   7080
agttatctgt cctcatttt atttattgtt ttttacaaaa agcatagaat a atgtgtgtt   7140
tcatgtgttt ggttagaggt tatagatgaa aagctttaat aataaatagt a gctaaatat   7200
acttcattgt ttgagtggta gaggagattt ttaaaattta tgaagactac a attctcttt   7260
catttcaaat aacatcccta ttttagtggt gagattaatg tatttgtttc t cttttctta   7320
ttttctttta tcaatattat atataaaact aaaatgcatc agtgtttac t atggattga   7380
tcataatgca attcactata aaataattga tgcttccctt aaaaaccaa a taattaaac   7440
aaacactcag ggttaatttt gtattttcat atctttattg catagtgtaa t tatttctat   7500
gtccttgaaa aaagaaaaaa aacactaggg tttttttaaa aagtttcat a ttttttttgt   7560
atagtgtaat tatcccactt tgggggccaa cttttttta cctaaggtaa a ggggtattt   7620
ttggtttttt tatgtttgtt ttttttgcaat tattatatgg gatcaagagt g ttatgatct   7680
tttttatataa aaaaaaaatg gttgacacgt gatctacaat tccccctccc t tttcattcc   7740
taaccttgaa agtcttagtg aaacatatag ttataataaa gaaatattat c tctagtttt   7800
gcaaattaat ttcataacat caattaaata ttctgataag gtaaagttat t taggatgga   7860
gaaatttaca taatgaagcc tccttctgcc tgagtagtgc atttctatgg t atttatgag   7920
catcaattct acaatccatt gaagcaaaag aactaaccct ctgaaaccc t cttgcagat   7980
aattgtgagt gaatgtaagt ccactacgaa atattcacac gattacgcac t tagttatca   8040
ttaaactttg ttttgggtgc tttgcatttt cttaattaga ttcttccaca g ctttccaat   8100
```

```
gcacattttg atgactttt ttatttatt tttcttgatg aaatgttga c atgattgca    8160
gtgtcaaatc aacaattgag aggtacaaaa aggcatctgc agattcttca a acactgggt  8220
ctgtttctga agccaatgct caggtaccat atatcagctc taactaacaa t ttgtactca  8280
taatatctat tagatggagt tcaagcataa tattcctccc aataatttat t gccaatata  8340
gtgctatgct accacttcat tcactctttc ttgataaccc cagcttgtat a aaatctatt  8400
agatacctct aagtttttgc cttacctttc tcactagtgt ctgacatgac a ctagtgttc  8460
acatggatta gcatctcgga gttgaaggtt gtctggcttc ttcgaanatc c aggg tttc  8520
aagaaggttt gtacattggg aggcccgtgg ttataaacct actgtgtaaa t ggtttgata  8580
aataatgatt catcagattt gagtaatagt cttttaattt ctttgtaaat g ttgtctatg  8640
tttttccag tcctccctac acacactctg ataattataa ccaattttgt t tcgcttcct  8700
cctttcgcta tgctcctact gaatttattt ccagtttgat tcagtattat a tgcatgttt  8760
acaagaaaat agaagggggg aatctacatc actgagattt tctacctgta t tttatcaac  8820
tgatctaata tgaacttgag gctcttaatt ttgttatata taatgtttta t tgccttttg  8880
ttcttgcatc tcagtactac cagcaagaag ctgccaagct gcgttcccaa a ttggtaatt  8940
tgcagaattc aaacaggtca gagcctgttt gatattgatc tatttgtcag a tgatatcgt  9000
tttctcttcc aaactccgct taagtataaa ttatatttca ggcatatgct g ggtgaagcg  9060
cttagttcat tgagtgtgaa ggaacttaag agtttggaaa tacgacttga g aaaggaata  9120
agcagaattc gttccaaaaa ggttttgata ctagtaccga attgatacta t cacattttt  9180
ttgttttact tggatatcac atttccatgt atggccatta acaagttttg t gttcatact  9240
ttcctgctat gtttctaaaa aattcctccc gcaaaccttg ccagaatgag c tgttgtttg  9300
cagaaatcga gtatatgcag aagagggtaa tgcttcttat gttatcacat t tcccattta  9360
tttaatattt attgttttct ggtggagtat attctatatg attgttatat a ttctgaggt  9420
aaaagtcatc tagtgtttat taacataatg attctatggt caacttattc c ttcctgttt  9480
tcactccgag atttteettt gattccttga atgaaaatgc acattacagg a ggttgactt  9540
gcacaacaat aaccagcttc tccgagcaaa ggtctttctt ctatctatct a tttatccat  9600
ctcgagtgag ggcaaggatg cgtgcgtgtg catgaatgaa gatctctatg t cttatatcg  9660
ttagtgagct gttttataatt tagaaatatg aggcttatct tgatagtgca g atttcagag  9720
aatgaaagaa agcgacagag catgaatttg atgccaggag gagcagactt t gagatcgtg  9780
cagtctcaac catatgactc tcggaactat tctcaagtga atggattaca g cctgcaagt  9840
cattactcac atcaagatca gatggcccct cagttagtgt aagtatctcc t ttgtaacga  9900
ataataggtt ttcattaacc ggacaaccag atttagtgtt gtgcattcat a aaatacaat  9960
taattacttt aatttggaga tgttccaaaa gttgcaactg catggttcat g ggctctaat  10020
ttcttggaag tatataaccg atgctatgtc ttttcattct cataattact g atcagtccc  10080
ttatagatga ttatttgcag attccttatga ccatttttccc attgagatta t aagatttg   10140
acatcgaata gttggactag gagtaaagag ctgttgctgt tatttagcac c ccaaaggaa  10200
atattatata cctctgaacc aattgaatgg ccgacctagg tttactgaaa t gtttagctg  10260
taagaaggtt aagtgttatc agattcccca agtgagaagt acatgtttct t agcatactt  10320
tatgtttcac gcaccttgat ttttcaaact ttgtttatcg atttctgaac t aaagtgact  10380
acattataga acttgaacct aaaattactc tcctcactat aggtgaaatc a gattacttg  10440
aaatactaca taaaaaaaat tatggcgttt gctggtattt ctaacatctt t tctgctaat  10500
```

-continued

```
cttgtattaa ttttctccta gatgaacttg ttattatgta aaaaggtttc a ttactcatg   10560 caatggtgca ctaatgcttg aggagttcca agtaactttg ctgtctcatg t aaagaagag   10620 tgctgaagtt cactatggtt taacttctac tgcactgctt gatattgcca t gaactctga   10680 catcatttgg cttgatcttg ttctaaaatc taaatgaaat aattctctct t actatatat   10740 cttcttaacc ctttgcatat gattaagtgg tctttgatag gatatcatta a aacctcgca   10800 taaaagctac cattttataa atttcaaact ccacgacgca ttttctggtg a ttccattgc   10860 tgattattgt ttaaagacat cattattcca attagtacat gtataataat t tcctctgtt   10920 gttggtgcag ttaataatct ccaagtgcag cagtttctcg catttccata t tccatggag   10980 agtacctggg tttccattga gcgcaaaagc tacatgtatg ctaaaaaacc t gaagtagcg   11040 taaatcatat ttgtctgggt gggagggcct agtactcttc ctctatgtat t aactatcct   11100 gtcccagtta agacataaga aatgtcagag aaggatttct tttctgtatg t ttcatgaag   11160 gcattaagat gctgttacag ttgtgactaa cttattatat atgtcttact g cttcatctt   11220 gtgatatttt cttgcatgtt aatctgatta agtgtagct tagaccattc a ccatgttaa   11280 tggtgacttg ttggtgacta ctagtagctg tagctctccg tagtactgct a tgccttcaa   11340 aaaatgatgg gtcggaaatt actagctagc tagtattgct gtttcattca a tctctgctt   11400 taacccaaaa atcaggacta gtggattagc ataccctctca ccaggacaat g cactagagc   11460 acattttcat cttcttctca tattt                                        11485
```

<210> SEQ ID NO 10
<211> LENGTH: 1219
<212> TYPE: DNA
<213> ORGANISM: Populus balsamifera subsp. trichoc arpa
<220> FEATURE:
<221> NAME/KEY: CDS
<222> LOCATION: (196)..(921)

<400> SEQUENCE: 10

```
tgagaggttg tttttcactt tataaatacc cacctcttag cccaaacttg c ttccatttt     60 cttcatctct ctactagtta gatttgtagg agaaatccca aaggaaaaga t cctcacttt    120 ctctacacat taactgctat ctacagcccc tagctacttt gttttatttc c tcccaagct    180 agctaggctg cagct atg gaa tat caa aat gaa tcc ctt gag agc tcc ccc      231
              Met Glu Tyr Gln Asn Glu Ser Leu Glu Ser Ser Pro
                1               5                  10 ctg agg aag ctg gga agg gga aag gtg gag a tc aag cgg atc gag aac      279
Leu Arg Lys Leu Gly Arg Gly Lys Val Glu I le Lys Arg Ile Glu Asn
         15                  20                  25 acc acc aat cgc caa gtc act ttc tgc aaa a gg cgc agt ggt ttg ctc      327
Thr Thr Asn Arg Gln Val Thr Phe Cys Lys A rg Arg Ser Gly Leu Leu
  30                  35                  40 aag aaa gcc tac gaa tta tct gtt ctt tgc g at gct gag gtt gca ctc      375
Lys Lys Ala Tyr Glu Leu Ser Val Leu Cys A sp Ala Glu Val Ala Leu
45                  50                  55                  60 atc gtc ttc tct agc cgc ggt cgc ctt tat g ag tac tct aac gat agt      423
Ile Val Phe Ser Ser Arg Gly Arg Leu Tyr G lu Tyr Ser Asn Asp Ser
                 65                  70                  75 gtc aaa tca aca att gag agg tac aaa aag g ca tct gca gat tct tca      471
Val Lys Ser Thr Ile Glu Arg Tyr Lys Lys A la Ser Ala Asp Ser Ser
         80                  85                  90 aac act ggg tct gtt tct gaa gcc aat gct c ag tac tac cag caa gaa      519
Asn Thr Gly Ser Val Ser Glu Ala Asn Ala G ln Tyr Tyr Gln Gln Glu
  95                 100                 105
```

```
gct gcc aag ctg cgt tcc caa att ggt aat t tg cag aat tca aac agg    567
Ala Ala Lys Leu Arg Ser Gln Ile Gly Asn L eu Gln Asn Ser Asn Arg
        110                 115                 120 cat atg ctg ggt gaa gcg ctt agt tca ttg a gt gtg aag gaa ctt aag    615
His Met Leu Gly Glu Ala Leu Ser Ser Leu S er Val Lys Glu Leu Lys
125                 130                 135                 140 agt ttg gaa ata cga ctt gag aaa gga ata a gc aga att cgt tcc aaa    663
Ser Leu Glu Ile Arg Leu Glu Lys Gly Ile S er Arg Ile Arg Ser Lys
                145                 150                 155 aag aat gag ctg ttg ttt gca gaa atc gag t at atg cag aag agg gag    711
Lys Asn Glu Leu Leu Phe Ala Glu Ile Glu T yr Met Gln Lys Arg Glu
        160                 165                 170 gtt gac ttg cac aac aat aac cag ctt ctc c ga gca aag att tca gag    759
Val Asp Leu His Asn Asn Asn Gln Leu Leu A rg Ala Lys Ile Ser Glu
                175                 180                 185 aat gaa aga aag cga cag agc atg aat ttg a tg cca gga gga gca gac    807
Asn Glu Arg Lys Arg Gln Ser Met Asn Leu M et Pro Gly Gly Ala Asp
190                 195                 200 ttt gag atc gtg cag tct caa cca tat gac t ct cgg aac tat tct caa    855
Phe Glu Ile Val Gln Ser Gln Pro Tyr Asp S er Arg Asn Tyr Ser Gln
205                 210                 215                 220 gtg aat gga tta cag cct gca agt cat tac t ca cat caa gat cag atg    903
Val Asn Gly Leu Gln Pro Ala Ser His Tyr S er His Gln Asp Gln Met
                225                 230                 235 gcc ctt cag tta gtt taa taatctccaa gtgcagcagt t tctcgcatt           951
Ala Leu Gln Leu Val
            240 tccatattcc atggagagta cctgggtttc cattgagcgc aaaagctaca t gtatgctaa  1011 aaaacctgaa gtagcgtaaa tcatatttgt ctgggtggga gggcctagta c tcttcctct  1071 atgtattaac tatcctgtcc cagttaagac ataagaaatg tcagagaagg a tttcttttc  1131 tgtatgtttc atgaaggcat taagatgctg ttacagttgt gactaactta t tatatatgt  1191 cttactgctt caaaaaaaaa aaaaaaa                                       1219

<210> SEQ ID NO 11
<211> LENGTH: 723
<212> TYPE: DNA
<213> ORGANISM: Populus balsamifera subsp. trichoc arpa
<220> FEATURE:
<221> NAME/KEY: CDS
<222> LOCATION: (1)..(723)

<400> SEQUENCE: 11 atg gaa tat caa aat gaa tcc ctt gag agc t cc ccc ctg agg aag ctg     48
Met Glu Tyr Gln Asn Glu Ser Leu Glu Ser S er Pro Leu Arg Lys Leu
1               5                   10                  15 gga agg gga aag gtg gag atc aag cgg atc g ag aac acc acc aat cgc     96
Gly Arg Gly Lys Val Glu Ile Lys Arg Ile G lu Asn Thr Thr Asn Arg
            20                  25                  30 caa gtc act ttc tgc aaa agg cgc agt ggt t tg ctc aag aaa gcc tac    144
Gln Val Thr Phe Cys Lys Arg Arg Ser Gly L eu Leu Lys Lys Ala Tyr
        35                  40                  45 gaa tta tct gtt ctt tgc gat gct gag gtt g ca ctc atc gtc ttc tct    192
Glu Leu Ser Val Leu Cys Asp Ala Glu Val A la Leu Ile Val Phe Ser
50                  55                  60 agc cgc ggt cgc ctt tat gag tac tct aac g at agt gtc aaa tca aca    240
Ser Arg Gly Arg Leu Tyr Glu Tyr Ser Asn A sp Ser Val Lys Ser Thr
65                  70                  75                  80 att gag agg tac aaa aag gca tct gca gat t ct tca aac act ggg tct    288
```

```
Ile Glu Arg Tyr Lys Lys Ala Ser Ala Asp S er Ser Asn Thr Gly Ser
            85                  90                  95 gtt tct gaa gcc aat gct cag tac tac cag c aa gaa gct gcc aag ctg        336
Val Ser Glu Ala Asn Ala Gln Tyr Tyr Gln G ln Glu Ala Ala Lys Leu
            100                 105                 110 cgt tcc caa att ggt aat ttg cag aat tca a ac agg cat atg ctg ggt        384
Arg Ser Gln Ile Gly Asn Leu Gln Asn Ser A sn Arg His Met Leu Gly
            115                 120                 125 gaa gcg ctt agt tca ttg agt gtg aag gaa c tt aag agt ttg gaa ata        432
Glu Ala Leu Ser Ser Leu Ser Val Lys Glu L eu Lys Ser Leu Glu Ile
        130                 135                 140 cga ctt gag aaa gga ata agc aga att cgt t cc aaa aag aat gag ctg        480
Arg Leu Glu Lys Gly Ile Ser Arg Ile Arg S er Lys Lys Asn Glu Leu
145                 150                 155                 160 ttg ttt gca gaa atc gag tat atg cag aag a gg gag gtt gac ttg cac        528
Leu Phe Ala Glu Ile Glu Tyr Met Gln Lys A rg Glu Val Asp Leu His
            165                 170                 175 aac aat aac cag ctt ctc cga gca aag att t ca gag aat gaa aga aag        576
Asn Asn Asn Gln Leu Leu Arg Ala Lys Ile S er Glu Asn Glu Arg Lys
            180                 185                 190 cga cag agc atg aat ttg atg cca gga gga g ca gac ttt gag atc gtg        624
Arg Gln Ser Met Asn Leu Met Pro Gly Gly A la Asp Phe Glu Ile Val
            195                 200                 205 cag tct caa cca tat gac tct cgg aac tat t ct caa gtg aat gga tta        672
Gln Ser Gln Pro Tyr Asp Ser Arg Asn Tyr S er Gln Val Asn Gly Leu
        210                 215                 220 cag cct gca agt cat tac tca cat caa gat c ag atg gcc ctt cag tta        720
Gln Pro Ala Ser His Tyr Ser His Gln Asp G ln Met Ala Leu Gln Leu
225                 230                 235                 240 gtt                                                                      723
Val <210> SEQ ID NO 12
<211> LENGTH: 241
<212> TYPE: PRT
<213> ORGANISM: Populus balsamifera subsp. trichoc arpa

<400> SEQUENCE: 12

Met Glu Tyr Gln Asn Glu Ser Leu Glu Ser S er Pro Leu Arg Lys Leu
1               5                   10                  15

Gly Arg Gly Lys Val Glu Ile Lys Arg Ile G lu Asn Thr Thr Asn Arg
            20                  25                  30

Gln Val Thr Phe Cys Lys Arg Arg Ser Gly L eu Leu Lys Lys Ala Tyr
        35                  40                  45

Glu Leu Ser Val Leu Cys Asp Ala Glu Val A la Leu Ile Val Phe Ser
    50                  55                  60

Ser Arg Gly Arg Leu Tyr Glu Tyr Ser Asn A sp Ser Val Lys Ser Thr
65                  70                  75                  80

Ile Glu Arg Tyr Lys Lys Ala Ser Ala Asp S er Ser Asn Thr Gly Ser
            85                  90                  95

Val Ser Glu Ala Asn Ala Gln Tyr Tyr Gln G ln Glu Ala Ala Lys Leu
            100                 105                 110

Arg Ser Gln Ile Gly Asn Leu Gln Asn Ser A sn Arg His Met Leu Gly
            115                 120                 125

Glu Ala Leu Ser Ser Leu Ser Val Lys Glu L eu Lys Ser Leu Glu Ile
        130                 135                 140

Arg Leu Glu Lys Gly Ile Ser Arg Ile Arg S er Lys Lys Asn Glu Leu
145                 150                 155                 160
```

```
Leu Phe Ala Glu Ile Glu Tyr Met Gln Lys Arg Glu Val Asp Leu His
                165                 170                 175

Asn Asn Asn Gln Leu Leu Arg Ala Lys Ile Ser Glu Asn Glu Arg Lys
            180                 185                 190

Arg Gln Ser Met Asn Leu Met Pro Gly Gly Ala Asp Phe Glu Ile Val
        195                 200                 205

Gln Ser Gln Pro Tyr Asp Ser Arg Asn Tyr Ser Gln Val Asn Gly Leu
    210                 215                 220

Gln Pro Ala Ser His Tyr Ser His Gln Asp Gln Met Ala Leu Gln Leu
225                 230                 235                 240

Val

<210> SEQ ID NO 13
<211> LENGTH: 10007
<212> TYPE: DNA
<213> ORGANISM: Populus balsamifera subsp. trichocarpa

<400> SEQUENCE: 13
tccattattt caacaataga ttcatttaca ctagcatgga tacttcaatg aataagaagt     60
gtgttattgt ttggagtaat agacacctat aattctcaaa ccttttactt tatttttatt    120
tcctttgtta tattacattt ttcatttctt tattgggttt tcattgacag gatggctaga    180
ttaatatagt ttcttgactt taataaataa aaaaaagatc aagactctct tcacaaacct    240
ttacaaaatt gggcgctata tctaaactaa aaaacttaag attatatact atctaaggag    300
tagcacacta taaataacat tataaaggta gtttgttgag cggaactaga ctttgcaaaa    360
taactttcca atatagcttt tcttgttgat gttgaccttt taatttagga tcaaacactt    420
gtaaattaca attaaaaggc ttattttttgt ttgccatttt taccaagcaa tgttaggatt    480
gctagagatt agttttttcca tggaataaga agttatcttt aaagggctta aaagacctag    540
tagcttgaca aggctatgac ttgtgttgtt ttggatcgta tggttattgt tatagaggtg    600
ctagtggtta aagacatcca tcatggaggt ggtgatgact aaaagagtt agatgtaaat    660 tggagactta tgttattctc acataaaaaa tgttagcctc cgacattgtt tttggatgtg    720
taaaatcaat gtaccatttt attcttcatt gttttgttttc cttattatga cttttacaaa    780
tttatccttt aggtgatgaa attccttcaa tcttgttcta tttttttttt taattcttgg    840
tacgtagttc tgtacttaat caagcaacat aaaatagtga tgccatcttc atcactctat    900
aaacgtggaa acccaaatct ctggctttta ttcatgatta aagtcatttc tagatttttt    960
tagacgttca agtgagattt agggttcaat aagagaggat caatggtgaa aatagaagaa   1020
caaagttgtt gtggttaagt tgactcggtg gttgttgagt tgggatatga aggaatagat   1080
ggtagactaa tctagtgttt ttgtccactt gagttcttaa ttattattcc atctccatga   1140
ctatttccat cttcttcttc agtgatattg tttatactct gtgatttggg ttattggaa   1200 cttattattg aggcagctca tccatagaaa tttggtactt gcttcaacaa accactaaaa   1260
tgttgtgtgg ttaatatttg agaatgcgcg aaaaaagcat cgtactaaat ttgggttccc    1320
gactggatga agagagatgt gattacttaa ttttatttgga ttttcggggt ttattagatt   1380
tttggaaagg taatacgata tcattggttt tgagaggaaa taacattggg attttgatga    1440
tttttgaata ataaaattaa gttttttctt gattcatttg ttaatagaaa gagaagaggg   1500
atagctctct tattctagca gaagtacgta tatgagctat gggatttaat tcttaatttt    1560
gtatgagtta ttgatcaaag aaaaagcaat gatgtgagaa gtctatatat ataatttctc   1620
```

```
ctacgtactc cgttgaacct tttttcctaa taaaaattga tagaaaatct a caacatata    1680 cagagaaatg tgaagttctt caattgagaa taaatcgttt caaaaggacg t aggaatctc    1740 cttgtagtga gtgaaactcc aagaaaatta acaacctgc tggggaacat c catacaact     1800 atcctccgat cccttctttt cttttcaagt aggcaggcaa taaaacgtat t tagcatagc    1860 caagttcaaa aaaaaaacaa gaagaagaag aagcaatgaa ataagggaaa a gatgaggtt    1920 ctcttgttaa gcacctttca tttgtaccat aattttgtcc ttggaatgat t agagagccc    1980 aaaaacgtgt tattcacccc agaaaatcc attttcaaaa agtcccttc t cttgatgac     2040 ctaaatcatt cacatggaag ccaaggaaga aaatgaaaaa aacgaatata g tggatggtt    2100 attgaggtct cagtcttcct atagcgtatt ctctaattaa ttccaagata a aaaaaaaa     2160 aaaattacaa ggatggtgta gataaactta gtagaaagta ttgttatata t atatatata    2220 tatatgggaa tggatgaaag gtcgtttatc acttttataa atgcccacct c ttagcccca    2280 acttgcttcc attttctgca tctctcctac tcagattcgt aggaacaaag a agagagaaa    2340 ccccagagca aaagatcctt actttctctc cttaataact actatctcta c aaccctac     2400 tttggtttat ttcctcccaa ggttagttac caaaacactg agacatatat c tcgttgtat    2460 tcttgagtgc ttcacttgtt tggggcttat caatcttctg atcttcttat c tcttcttca    2520 tcatagtgac tgaggaaccc catcagatga aacttttaat tttctaaaaa a gatttactt    2580 acaaacgttt ctgtcactct ctgccgtttc aatctcccaga ttgaagcatt a ctagttcat   2640 ccctttgttt tgtttctcaa ttattttcat atccatgaaa ccataacaag g gctaattca   2700 agagctagct gcaggcgttc atggaacccc tttcttctgt ttattttgtc t tccatcatg   2760 agctattcag tgctcaagag tattcctgct aaatatgcta tgaattatcc t tatatataa   2820 atcattcttg aattaattac tagctagtag ttcagtaatt ttattactct c ttttctgct   2880 gtcttcaccc agtttgtgtt ttggatcagc tagctaggca gcagctatgg c ataccaaaa   2940 tgaaccccaa gagagctctc ccctgaggaa gctggggagg ggaaaggtgg a gatcaagcg   3000 gatcgagaac accaccaatc gccaagtcac tttctgcaaa aggcggaatg g tttgctcaa   3060 gaaagcctat gaattatctg ttctttgcga tgctgaggtt gcactcatcg t cttctccag   3120 ccgtggacgc ctttatgagt actctaacaa taggtatata cttagttcct c ggctcatga   3180 attctccatg ttgcaaaccc tcttcaagtg ctcaaagttg gttttttcttg c tttctcatc   3240 caaagggatt tgtttttttct ttttgcttat gtcagtgtta attttttattg c tttggtttt   3300 gagctgtttc tttaattggt tttcttccat catcattttc tttcttcaat t ggttttcaa   3360 cgtttgttgt ggggaaaaaa aataggagcc tggtgtcaag gtttttagct t ctgagctag   3420 atcttcgggt gtctttaaag taaaagaaca caatcattct ttatgctgca g tttggattg   3480 aatttcttct caaaatacaa ttcacttgtc tttctttctt ctatttcttt t cttttcctt   3540 gtataagcat aattaatgtt ttgttttttcc ttttctttat ttcaccctta g atgattgtg   3600 atgcatacat gattttgagt tcttggtaca tagatctggt gtattagata g acatagaag   3660 cacaattata agtgtaataa ggtagtagaa acaagtagag ggctgggaaa a tgtatgcag   3720 gcatgtgata tcagcctctt tatctcctcc cttgatgtta agtttgctgt t tccttttc    3780 tttcttttcc atcattcctc ttgaactctg cctctctcct ttactctttt c ttgcacata   3840 catgcatgtt tgagtcatct ctagggctaa agagattacc tatagctaaa g ctgtcatct   3900 tctcattagt ccaaaccctc ccatctcttc tcacttccaa aatagcacgt c agtcggaca   3960
```

-continued

```
taagaagaaa agagtacaaa gtcaaattaa atgtgaaaaa aaaagaaagg g ttttttat    4020 atgtcatgtc accaaacaca caaacatata ttactagggt ttcaaaatcc a aatccccaa    4080 atgggtttct tcatcttatt ttattttcc aaaacaatca ctaggatctc t caatttagg    4140 attcttttc ctctaattca cacgaatttc acaaaatctc tgttcgaacc c acgtgggga    4200 aagtgaaaag cttttgttt ttcaagcata gccctagtta gggttcatat t taagtaacc    4260 acttgaagtc atcaaaattg aaccgaaact ttagtgcaaa ctattcaatc a accatgtgg    4320 attcttccat aaccagtcaa aaattaagtt agatttcacc tagatttta c cctttttaa    4380 cctcggtaag aagggtacag taactggtta gggtttaata gccagttcaa t atatcagat    4440 tgttgttttg gtttatgaaa agaatctttg gtcacgtcac acacgattt t cagttcttg    4500 actactgaca aaagggttca agtcatgatt catgaaaatg aaccataaat t ttgaactcc    4560 caatctgcaa aaaaaagaa gaagaagcaa taccacacag aatattgtcc a tttcttctc    4620 cttagatccc tccctctctc tgttattttc tttcccatag tgaaagagag a tggaacaac    4680 gagaaagggt tagctaaggt catgatgatg ccattgttgg tcattgttga g tgtggtttg    4740 cgtttgttca agatcttgaa tatatgtatg tatgtatgtg tatgtatgta c gcaagttct    4800 tttaggaaga gagagttaat acagagagag aaagagaaga gacgatgtac g acaagtgct    4860 agccaatggg agacttctgt caattttggc ttttttaatg taaatagaag c gtaaaactc    4920 tagcagctgc tgctgctgct cctctctgag agtttcagtc acattcaaga a aacaaaaaa    4980 aaataatttt ttatcttatt acaaatgaaa tagaatatcg aggtgggtaa t agatggtgg    5040 ctcaagagat tatccaccat agaagaaaaa aagaaaaata gatattgccc a ccatgtaat    5100 gaggaattga caagtgggat agatgtgacc gttgatttag cttggccaat c atgttatag    5160 gactcagtga cagcttggca gagacagcca atcactggct cgacgaagtt a aggtatcag    5220 aaaatctaga tatctgggtc ttgtcttaat tgacaaaatg tgttcacatc t tactgttat    5280 tattatggca aaattttagg atgcacaaag aactgggtgg aggttttccc a tccatcttc    5340 ttctttaggg ttttaaatga gttaacttaa tggagttatt agttgatttg a ctctttgat    5400 ttgaatgttc ttaccttaaa atcatggctt aacatcatcc ggtgttggta c aggggcatg    5460 attttgctct ctccctcttc agtcaatttc atcatttatt ttgatatata a ttttctttt    5520 tccctaatgt taagcctcta ctgtcacatc tttaaattac tagagggata t gtaactgat    5580 aactagtaac ttcacataaa atactgtaca atatagattt aaaaaaggaa t tttatataa    5640 aatttgaact ctcaattta ttttatttt gttatttgga tgagtagttt g tctaaagca    5700 atagctaata tggagggtat taagaaactg cctctagttg ttgacacaaa a gccttgaag    5760 cacgtatttt actcgctaat tcacacttct tggctgtgct cttaccatct t ggaaaataa    5820 atggatttca aaaagtaca tggtttctta atctatttga aatgatttaa t aatgaaaaa    5880 taaaatcaaa tgtaaagtct taaatgtaat aaaaaataat tttcgatgtt t tttgagtgt    5940 ttttttttt ataattttga aatcttcata tttatatgtc catataaaac a taggaaaaa    6000 tcatcaattc tcaaaattat tggagaaaaa cacctacata tgcattatcg a tcaactaca    6060 caaataggaa gtaaccattc gaagaaaatt aaagactaga gacatcaaaa g ttgacaaac    6120 atgtgtacat gtgttaatgt aatcgtgtgc aagtgtcatg tcagttgagt t accagtgct    6180 aagtgttgct tccgttaatg ttataacaaa ttatcaatat atgtaagtac t aattttaaa    6240 gaatattgct attaaatagt aattaagcta tctttggata catagaagac c atgggaagt    6300 gaaaagtttc cttgataaaa ggagttgtgg ttttcaatat atatatatat t caagaatga    6360
```

```
catgagaagt ctcttaatac aggcctccaa tgaaaaggaa atgaagaata a ttttccaat    6420 tactttcgag taaaaagtta tctatgttca atattttctt ttctttaaaa a aaagagaga    6480 acagaataga agaatgtata gatctgtctg ttttttgttc tttgataact a gaatagtgt    6540 atgtttcagt ttcttggtaa gaggttagat gtgaagttct tataatacta t aacaaaata    6600 tacttcatca tttgaggggt ggaggagatc ttacaaacaa actactgaac c caattccct    6660 tttactttta gtaacatccc aattttggtg ttgagatatt gtgataaggt a aagttatat    6720 actttggcca aagtaattta caggatgaag ccttcttctc cctgattagt g actttctga    6780 ggtattaaca tcagagttct gaagattatc caaaaaaaca tcagagttct g aaatttatt    6840 agggccagag atttaatatt cttgaaatcc tcaattgcag ataattatga a atttaagat    6900 caaaatgaaa tatccacagg atcacttatt tatgactaaa atttgttttt g gggtgacat    6960 tcttccacat tattagaatg cacgttgtga tgacacttgc tttttcttga t ggaaatgat    7020 gacatgaatg cgcagtgtca aatctacaat tgaaaggtac aaaaaggcat g tgcagattc    7080 ttccaacaac gggtcagttt ctgaagccaa tgctcaggta tcatttatca g ctctaacaa    7140 ttgtttacat gtgcagattc ttccaacact tgttataat cctttgtgtc c tactggttt    7200 ttggttttgg atactgatta gtttgtaatg tatgcactag ggctgaaaaa a ggcatacag    7260 aattatgata ttatagaaca aaattaccaa ttaacagtat ttttctttct t ttttaataa    7320 attacagtat agttttttcgt gaatttatgt gcgatcgagt gtttacactg a atttcaaaa    7380 tgtgcatgta cgttttgagg ctagtgtaga accacagaaa gacagtatat a tggaactac    7440 cagcatataa caaaatcctt tttatgaaat tttatcgtcg atgttttaca c taaattctc    7500 tcactattca ttaacagcgt aattaacaac atgctgttaa attatagaag g agttcaagc    7560 aatattccta acaatcattt attgccaata tttgtcaaat acccttttgtg a taacctcat    7620 ttgtgtaaaa tcgattaaat acatacctat ttaattttgc ttctcagagt g gaggttttt    7680 tcctactgca ttgggagtca tgagtgtaaa cctgcattat agccagtttt g tgtacagaa    7740 accctttttcc ttcctctgtt gctgtggccc tattgtatca atttatttcc a gtttgattc    7800 ggtattatat acatgtttcc aagaagtata agagagaaat gtacatcact g atattttct    7860 acttatattt tgagttctaa tctgaactcg aggatcttaa tctagttatt t ataatgttt    7920 tattgccttt tgcttttgca tttcagtttt atcagcaaga agctgccaag c tgcgctcgc    7980 aaattggtaa tttgcagaat tcaaacaggt atgatcattt gtgatcttga t caatttgtt    8040 agataaaatt tgttttttcct cttccaaact ccgtttaagc aaattaattt t caggaatat    8100 gctgggtgaa tcacttagtg cattgagtgt gaaggaactt aagagcttgg a gataaaact    8160 tgagaaagga attggtagaa ttcgttcgaa aaaggtcttt attctagtac t caaatgatt    8220 ctctcttttt ttaagtcaaa tatcacttta attttccttg tattgccact a acaagtttt    8280 gttttgtctt gttttccttt tgttttttaa ttcctccctc aaacctgcca g aatgagctg    8340 ttgtttgctg aaattgagta tatgcagaag agggtaacaa cttttgtgct c atattcacc    8400 atgacttctt ctatttgaga taaaaaatc aagttttgc caatttaatg a tcctatggt    8460 gaacctcttc tattgtattt tcactccaaa aattttcttt gattcattga a tgaaaatgc    8520 aaattgcagg agattgactt gcacaacaat aaccagcttc tccgagcaaa g gtctttcta    8580 cttatctatt tatcaatgcc ttgtgtgtgt ctgaacttgg atcttaatat c ttagatcgt    8640 tggtgggttg ttttttattta gtaaatatga cactacgtgg ggcttatgtt g atgttgcag    8700
```

-continued

```
attgcagaga atgaaagaaa gcgacagcac atgaatttga tgccgggagg t gtcaacttc    8760 gagatcatgc agtctcaacc atttgactct cggaactatt ctcaagttaa t ggattgccg    8820 cctgccaatc attaccctca tgaagaccag ctcttcagtt agtgtaagta t ttcctttgc    8880 aatgagctgt agttttcat caattaatta ctgatgagca tataattaac t actttgatc    8940 tggatgggtt tcagtagcag cagcggctga atggttcgtg gtctgtaaaa a tttattgga    9000 aggatataat aactgatgct gtgccttcta attctcataa tcatttgatc t ttcaattag    9060 ttagatgatg atttacgcat tcttattgag atttttacca ttggatgata a gagggaatt    9120 gcaatattta gctgttgtac taaaagtaga ctgctgttat cagcacccca t gctcactga    9180 agaactagaa gattacccaa cctagtttta cttcactgaa ccgtttgcat g caagaactt    9240 aaagcgtaat ctgatttccc aagtgacaag tatatgtttc taactccttg a cgaatctgc    9300 tgctgattcc tttgctggtt tatattattc ttatgactac aaacacaata c ttttcaact    9360 agctagtgaa tgaataatca tttccttatg ttgcagttaa aaagcaccaa g tgcagcaac    9420 tcctcgcatt tccatattcc atggagagta cctactattt cactgagcgc a aaagctgca    9480 agtacgctaa aacaaaaatc tgaagtagca taactcaaat ttgtgccggt g gagagccta    9540 gtactcttcc tccatgtatt gcttttccag tcccagttaa gacataacaa a tgtcagata    9600 aggatttctt ttctgcatgt ttcatgaagg cactaagatg ctgtgacagt a cttgtgact    9660 aacttattat atattttgtc ttatatttct tatctttcat cttgtaatat t tcttcgcgt    9720 atctagtatt gcttttcatt caaacccttc cgtgacccag aatcaggacc a ctgccttag    9780 catgctgttc atcagcggta catgtaatag aggcctctat attttgctgc c agcttaata    9840 tacagtttac atctttcatg tgtgagttca gcacgagtaa ttaattttat g gttattttc    9900 tttgtaacag agcctcttga tgtctatttg taagcattgc gaggttttta a agattaaat    9960 taatacgtaa gctgaatgtc tcgcaaaagg tacaaattgc ttcagct             10007
```

<210> SEQ ID NO 14
<211> LENGTH: 1159
<212> TYPE: DNA
<213> ORGANISM: Populus balsamifera subsp. trichoc arpa
<220> FEATURE:
<221> NAME/KEY: CDS
<222> LOCATION: (99)..(815)

<400> SEQUENCE: 14

```
gaaaccccag agccaaagat ccttactttc tctccttaat aactactatc t ctacatccc     60 ctactttggt ttatttcctc ccaagctagg cagcagct atg gca tac caa aat gaa    116
                                         Met Ala Tyr Gln Asn Glu
                                         1               5 ccc caa gag agc tct ccc ctg agg aag ctg g gg agg gga aag gtg gag    164
Pro Gln Glu Ser Ser Pro Leu Arg Lys Leu G ly Arg Gly Lys Val Glu
         10                  15                  20 atc aag cgg atc gag aac acc acc aat cgc c aa gtc act ttc tgc aaa    212
Ile Lys Arg Ile Glu Asn Thr Thr Asn Arg G ln Val Thr Phe Cys Lys
     25                  30                  35 agg cgg aat ggt ttg ctc aag aaa gcc tat g aa tta tct gtt ctt tgc    260
Arg Arg Asn Gly Leu Leu Lys Lys Ala Tyr G lu Leu Ser Val Leu Cys
 40                  45                  50 gat gct gag gtt gca ctc atc gtc ttc tcc a gc cgt gga cgc ctt tat    308
Asp Ala Glu Val Ala Leu Ile Val Phe Ser S er Arg Gly Arg Leu Tyr
55                  60                  65                  70 gag tac tct aac aat agt gtc aaa tct aca a tt gaa agg tac aaa aag    356
Glu Tyr Ser Asn Asn Ser Val Lys Ser Thr I le Glu Arg Tyr Lys Lys
                 75                  80                  85
```

```
gca tgt gca gat tct tcc aac aac ggg tca g tt tct gaa gcc aat gct       404
Ala Cys Ala Asp Ser Ser Asn Asn Gly Ser V al Ser Glu Ala Asn Ala
                90                  95                 100 cag ttc tat cag caa gaa gct gcc aag ctg c gc tcg caa att ggt aat       452
Gln Phe Tyr Gln Gln Glu Ala Ala Lys Leu A rg Ser Gln Ile Gly Asn
            105                 110                115 ttg cag aat tca aac agg aat atg ctg ggt g aa tca ctt agt gca ttg       500
Leu Gln Asn Ser Asn Arg Asn Met Leu Gly G lu Ser Leu Ser Ala Leu
        120                 125                 130 agt gtg aag gaa ctt aag agc ttg gag ata a aa ctt gag aaa gga att       548
Ser Val Lys Glu Leu Lys Ser Leu Glu Ile L ys Leu Glu Lys Gly Ile
135                 140                 145                 150 ggt aga att cgt tcg aaa aag aat gag ctg t tg ttt gct gaa att gag       596
Gly Arg Ile Arg Ser Lys Lys Asn Glu Leu L eu Phe Ala Glu Ile Glu
                155                 160                 165 tat atg cag aag agg gag att gac ttg cac a ac aat aac cag ctt ctc       644
Tyr Met Gln Lys Arg Glu Ile Asp Leu His A sn Asn Asn Gln Leu Leu
            170                 175                 180 cga gca aag att gca gag aat gaa aga aag c ga cag cac atg aat ttg       692
Arg Ala Lys Ile Ala Glu Asn Glu Arg Lys A rg Gln His Met Asn Leu
        185                 190                 195 atg ccg gga ggt gtc aac ttc gag atc atg c ag tct caa cca ttt gac      740
Met Pro Gly Gly Val Asn Phe Glu Ile Met G ln Ser Gln Pro Phe Asp
200                 205                 210 tct cgg aac tat tct caa gtt aat gga ttg c cg cct gcc aat cat tac      788
Ser Arg Asn Tyr Ser Gln Val Asn Gly Leu P ro Pro Ala Asn His Tyr
215                 220                 225                 230 cct cat gaa gac cag ctc ttc agt tag tttaaaaa gc accaagtgca            835
Pro His Glu Asp Gln Leu Phe Ser
                    235 gcaactcctc gcatttccat attccatgga gagtacctac tatttcactg a gcgcaaaag    895 ctgcaagtac gctaaaacaa aaatctgaag tagcataact caaatttgtg c cggtggaga    955 gcctagtact cttcctccat gtattgcttt tccagtccca gttaagacat a acaaatgtc   1015 agataaggat ttcttttctg catgtttcat gaaggcacta agatgctgtg a cagtacttg   1075 tgactaactt attatatatt ttgtcttata tttcttaaaa aaaaaaaaa a aaaaaaaa     1135 aaaaaaaaaa aaaaaaaaaa aaaa                                           1159

<210> SEQ ID NO 15
<211> LENGTH: 714
<212> TYPE: DNA
<213> ORGANISM: Populus balsamifera subsp. trichoc arpa
<220> FEATURE:
<221> NAME/KEY: CDS
<222> LOCATION: (1)..(714)

<400> SEQUENCE: 15 atg gca tac caa aat gaa ccc caa gag agc t ct ccc ctg agg aag ctg       48
Met Ala Tyr Gln Asn Glu Pro Gln Glu Ser S er Pro Leu Arg Lys Leu
  1               5                  10                  15 ggg agg gga aag gtg gag atc aag cgg atc g ag aac acc acc aat cgc       96
Gly Arg Gly Lys Val Glu Ile Lys Arg Ile G lu Asn Thr Thr Asn Arg
             20                  25                  30 caa gtc act ttc tgc aaa agg cgg aat ggt t tg ctc aag aaa gcc tat      144
Gln Val Thr Phe Cys Lys Arg Arg Asn Gly L eu Leu Lys Lys Ala Tyr
         35                  40                  45 gaa tta tct gtt ctt tgc gat gct gag gtt g ca ctc atc gtc ttc tcc      192
Glu Leu Ser Val Leu Cys Asp Ala Glu Val A la Leu Ile Val Phe Ser
     50                  55                  60
```

-continued

```
agc cgt gga cgc ctt tat gag tac tct aac a at agt gtc aaa tct aca     240
Ser Arg Gly Arg Leu Tyr Glu Tyr Ser Asn Ser Val Lys Ser Thr
 65                  70                  75                  80 att gaa agg tac aaa aag gca tgt gca gat t ct tcc aac aac ggg tca     288
Ile Glu Arg Tyr Lys Lys Ala Cys Ala Asp Ser Ser Asn Asn Gly Ser
                 85                  90                  95 gtt tct gaa gcc aat gct cag ttc tat cag c aa gaa gct gcc aag ctg     336
Val Ser Glu Ala Asn Ala Gln Phe Tyr Gln Gln Glu Ala Ala Lys Leu
            100                 105                 110 cgc tcg caa att ggt aat ttg cag aat tca a ac agg aat atg ctg ggt     384
Arg Ser Gln Ile Gly Asn Leu Gln Asn Ser Asn Arg Asn Met Leu Gly
        115                 120                 125 gaa tca ctt agt gca ttg agt gtg aag gaa c tt aag agc ttg gag ata     432
Glu Ser Leu Ser Ala Leu Ser Val Lys Glu Leu Lys Ser Leu Glu Ile
    130                 135                 140 aaa ctt gag aaa gga att ggt aga att cgt t cg aaa aag aat gag ctg     480
Lys Leu Glu Lys Gly Ile Gly Arg Ile Arg Ser Lys Lys Asn Glu Leu
145                 150                 155                 160 ttg ttt gct gaa att gag tat atg cag aag a gg gag att gac ttg cac     528
Leu Phe Ala Glu Ile Glu Tyr Met Gln Lys Arg Glu Ile Asp Leu His
                165                 170                 175 aac aat aac cag ctt ctc cga gca aag att g ca gag aat gaa aga aag     576
Asn Asn Asn Gln Leu Leu Arg Ala Lys Ile Ala Glu Asn Glu Arg Lys
            180                 185                 190 cga cag cac atg aat ttg atg ccg gga ggt g tc aac ttc gag atc atg     624
Arg Gln His Met Asn Leu Met Pro Gly Gly Val Asn Phe Glu Ile Met
        195                 200                 205 cag tct caa cca ttt gac tct cgg aac tat t ct caa gtt aat gga ttg     672
Gln Ser Gln Pro Phe Asp Ser Arg Asn Tyr Ser Gln Val Asn Gly Leu
    210                 215                 220 ccg cct gcc aat cat tac cct cat gaa gac c ag ctc ttc agt             714
Pro Pro Ala Asn His Tyr Pro His Glu Asp Gln Leu Phe Ser
225                 230                 235
```

<210> SEQ ID NO 16
<211> LENGTH: 238
<212> TYPE: PRT
<213> ORGANISM: Populus balsamifera subsp. trichoc arpa

<400> SEQUENCE: 16

```
Met Ala Tyr Gln Asn Glu Pro Gln Glu Ser Ser Pro Leu Arg Lys Leu
 1               5                  10                  15

Gly Arg Gly Lys Val Glu Ile Lys Arg Ile Glu Asn Thr Thr Asn Arg
                20                  25                  30

Gln Val Thr Phe Cys Lys Arg Arg Asn Gly Leu Leu Lys Lys Ala Tyr
             35                  40                  45

Glu Leu Ser Val Leu Cys Asp Ala Glu Val Ala Leu Ile Val Phe Ser
     50                  55                  60

Ser Arg Gly Arg Leu Tyr Glu Tyr Ser Asn Ser Val Lys Ser Thr
 65                  70                  75                  80

Ile Glu Arg Tyr Lys Lys Ala Cys Ala Asp Ser Ser Asn Asn Gly Ser
                 85                  90                  95

Val Ser Glu Ala Asn Ala Gln Phe Tyr Gln Gln Glu Ala Ala Lys Leu
            100                 105                 110

Arg Ser Gln Ile Gly Asn Leu Gln Asn Ser Asn Arg Asn Met Leu Gly
        115                 120                 125

Glu Ser Leu Ser Ala Leu Ser Val Lys Glu Leu Lys Ser Leu Glu Ile
    130                 135                 140
```

```
Lys Leu Glu Lys Gly Ile Gly Arg Ile Arg S er Lys Lys Asn Glu Leu
145                 150                 155                 160

Leu Phe Ala Glu Ile Glu Tyr Met Gln Lys A rg Glu Ile Asp Leu His
            165                 170                 175

Asn Asn Asn Gln Leu Leu Arg Ala Lys Ile A la Glu Asn Glu Arg Lys
        180                 185                 190

Arg Gln His Met Asn Leu Met Pro Gly Gly V al Asn Phe Glu Ile Met
    195                 200                 205

Gln Ser Gln Pro Phe Asp Ser Arg Asn Tyr S er Gln Val Asn Gly Leu
    210                 215                 220

Pro Pro Ala Asn His Tyr Pro His Glu Asp G ln Leu Phe Ser
225                 230                 235

<210> SEQ ID NO 17
<211> LENGTH: 27
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 17
atgggtcgtg gaaagattga aatcaag                                         27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 18
atttgtgaaa aagagctttt atattta                                         27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 19
aggaaggcga agttcatggg atccaaa                                         27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 20
tccacatcga caaagaagat ctacgat                                         27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial  Sequence:
      oligonucleotide primer
```

```
<400> SEQUENCE: 21
gtcactttct gcaaaaggcg cagtggt                                        27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 22
aactaactga agggccatct gatcttg                                        27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 23
atggaatatc aaaatgaatc ccttgag                                        27

<210> SEQ ID NO 24
<211> LENGTH: 29
<212> TYPE: DNA
<213> ORGANISM: Artificial Sequence
<220> FEATURE:
<223> OTHER INFORMATION: Description of Artificial  Sequence:
      oligonucleotide primer

<400> SEQUENCE: 24
attcatgctc tgtcgctttc tttcattct                                      29
```